US008299229B2

(12) United States Patent
Tang et al.

(10) Patent No.: US 8,299,229 B2

(45) Date of Patent: Oct. 30, 2012

(54) MUCIN ANTIGEN VACCINE

(75) Inventors: Yucheng Tang, San Diego, CA (US); Albert Deisseroth, San Diego, CA (US)

(73) Assignee: MicroVAX, LLC, Manassas, VA (US)

( * ) Notice: Subject to any disclaimer, the term of this patent is extended or adjusted under 35 U.S.C. 154(b) by 399 days.

(21) Appl. No.: 10/997,055

(22) Filed: Nov. 23, 2004

(65) Prior Publication Data

US 2005/0226887 A1 Oct. 13, 2005

Related U.S. Application Data

(60) Provisional application No. 60/524,925, filed on Nov. 24, 2003, provisional application No. 60/525,552, filed on Nov. 25, 2003, provisional application No. 60/529,015, filed on Dec. 11, 2003.

(51) Int. Cl.
*C07H 21/04* (2006.01)
*A61K 39/00* (2006.01)
*A61K 39/12* (2006.01)

(52) U.S. Cl. .................. 536/23.4; 424/192.1; 424/199.1

(58) Field of Classification Search .................... 514/44; 536/23.4; 424/192.1, 199.1
See application file for complete search history.

(56) References Cited

U.S. PATENT DOCUMENTS 4,161,519 A 7/1979 Talwar
4,608,251 A 8/1986 Mia
5,658,785 A 8/1997 Johnson
5,849,522 A 12/1998 Fleckenstein et al.
5,849,876 A 12/1998 Linsley et al.
5,874,085 A 2/1999 Mond et al.
5,928,913 A 7/1999 Efstathiou et al.
5,962,406 A 10/1999 Armitage et al.
6,017,527 A 1/2000 Maraskovsky et al.
6,040,174 A 3/2000 Imler et al.
6,087,329 A 7/2000 Armitage et al.
6,110,744 A 8/2000 Fang et al.
6,133,029 A 10/2000 Gruber et al.
6,147,055 A 11/2000 Hobart et al.
6,218,140 B1 4/2001 Fleckenstein et al.
6,224,870 B1 5/2001 Segal
6,287,557 B1 9/2001 Boursnell et al.
6,290,972 B1 9/2001 Armitage et al.
6,294,654 B1 9/2001 Bogen et al.
6,440,944 B2 8/2002 Bruder et al.
6,482,407 B2 11/2002 Soo Hoo
6,497,876 B1 12/2002 Maraskovsky et al.
6,500,641 B1 12/2002 Chen et al.
6,566,128 B1 5/2003 Graham et al.
6,632,436 B2 10/2003 Segal
6,794,188 B2 9/2004 Barsov et al.
6,923,958 B2 8/2005 Xiang et al.
7,067,110 B1 * 6/2006 Gillies et al. ................ 424/1.49
7,118,751 B1 10/2006 Ledbetter et al.
2003/0176377 A1 9/2003 Xiang et al.
2005/0226888 A1 10/2005 Deisseroth et al.
2006/0286074 A1 12/2006 Tang et al.
2007/0128223 A1 6/2007 Tang et al.
2007/0269409 A1 11/2007 Deisseroth et al.

FOREIGN PATENT DOCUMENTS

WO WO 96/11279 4/1996
WO WO 98/17799 4/1998
WO WO 01/56602 A2 8/2001
WO WO 2004/044176 5/2004

OTHER PUBLICATIONS

Grinstead, Biochemistry, 41:9946-9961, 2002.*
Rolph et al, Current Opinions in Immunology, 9:517-524, 1997.*
Mitchell, Current Opinions Investigative Drugs, 3:150-158, 2002.*
Parkinson, JF et al. J Biol Chem 265(21):12602-12610, 1990.*
Fanslow, WC et al. Sem Immunol 6:267-278, 1994.*
Cooper, G.M. III. Cell Structure and Function, 12. The Cell Surface, The Cell: A Molecular Approach. Sunderland, MA: Sinauer Associates, Inc, 2000. This reference was obtain from the interest at http://www.ncbi.nlm.nih.gov/books/bv.fcgi?highlight=structure,plasma membrane&rid=cooper.section.1967 (1 of 5) Feb. 5, 2008 6:28:21 PM and comprises pp. 1-5.*
Addgene pp. 1-3 was obtained from the internet at http://www.addgene.org/pgvec1?f=c&cmd=showvecinfo&vectorid=29 (2 of 4)Feb. 5, 2008 2:20:53 PM.*
Leitner et al. Blood 113(1):37-45, 2008.*
McDonell et al. Clincal and Developmental Immunology. vol. 2010, Article ID 539519, pp. 1-9, dio:10.1155/2010/539519, 2010.*
Andrianifahanana, et al., "Mucin (MUC) Gene Expression in Human Pancreatic Adenocarcinoma and Chronic Pancreatitis: A Potential Role of MUC4 as a Tumor Marker of Diagnostic Significance," *Clin Cancer Res.* 7:4033-4040 (2001).
Arai, et al., "Design of the linkers which effectively separate domains of a bifunctional fusion protein," *Protein Engineering*, 14(8):529-532 (2001).
Baruch, et al., "The Breast Cancer-associated MUC1 Gene Generates Both a Receptor and Its Cognate Binding Protein," *Cancer Res.*, 59:1552-1561 (1999).
Bieche, et al., "A gene dosage effect is responsible for high overexpression of the MUC1 gene observed in human breast tumors," *Cancer Genet. Cytogenet.* 98:75-80 (1997).
Byars, et al., "Adjuvant formulation for use in vaccines to elicit both cell-mediated and humoral immunity," *Vaccine* 5:223-228 (1987).
Chen, et al., Linkage of CD40L to a self-tumor antigen enhances the antitumor immune responses of dendritic cell-based treatment. Cancer Immunology Immunother. 51(6) :341-348, 2002.
Choudhury, et al., Dendritic cells derived in vitro from acute myelogenous leukemia cells stimulate antologous, antileukemic T-cell responses. Blood, 93(3) : 780-786, 1999.

(Continued)

*Primary Examiner* — Marcia S Noble
(74) *Attorney, Agent, or Firm* — Jacob Frank; Glenn Snyder

(57) ABSTRACT

Provided are expression vectors for generating an immune response to a mucin. The vectors comprise a transcription unit encoding a secretable polypeptide, the polypeptide comprising a secretory signal, a mucin antigen and CD40 ligand. Also provided are methods of generating an immune response against cells expressing a mucin by administering an effective amount of the vector. Further provided are methods of generating an immune response against cancer cells expressing a mucin in an individual by administering an effective amount of the vector. Still further provided are methods of overcoming anergy to a mucin self antigen by administering an effective amount of the vector.

30 Claims, 3 Drawing Sheets

OTHER PUBLICATIONS

Dakappagari et al., "Chimeric multi-human epidermal growth factor receptor-2 B cell epitope peptide vaccine mediates superior antitumor responses," *J Immuno.* 170(8):4242-4253 (2003).
Dhodapkar, et al. "Rapid generation of broad T-cell immunity in humans after a single injection of mature dendritic cells," *J Clin Invest.* 104:173-180 (1999).
Eck and Turka, Generation of protective immunity against an immunogenic cacinoma requires CD40/CD40L and B7/CD28 interactions but not CD4+ T cells. Cancer Immunology Immunother, 48:336-341, 1999.
Engelmann, et al., Identification and topology of variant sequences within individual repeat domains of the human epithelial tumor mucin MUC1. J. Biol. Chem. 276:27764-27769 , 2001.
Filipe, MI, "Mucins and gastrointestinal malignancy:A new approach to the interpretation of biopsies," *Acta Med Port* 1:351-365 (1979).
Filipe, MI, "Mucins in the human gastrointestinal epithelium: a review," *Invest Cell Pathol* 2:195-216 (1979).
Fong, et al. "Dendritic Cells Injected Via Different Routes Induce Immunity in Cancer Patients," *J Immunol.* 166:4254-4259 (2001).
Freund, "The mode of action of immunologic adjuvants," *Adv. Tuberc. Res.* 7:130-148 (1956).
Garcon et al., "Universal vaccine carrier. Liposomes that provide T-dependent help to weak antigens," *J. Immunol.* 146:3697 (1991).
Gendler S.J. et al, "Molecular cloning and expression of human tumor-associated polymorphic epithelial mucin," *J. Biol. Chem.* 265:15286-15293 (1990).
Gong, et al., "Selection and characterization of MUCI-specific CD8+ cells from MUCI transgenic mice immunized with dendritic-carcinoma fusion cells." *Immunology*, 101:316-324 (2000).
Greenlee, et al., "Cancer statistics, 2000," *Cancer J.* 50:7-33 (2000).
Gunzer, et al., "Dendritic cells and tumor immunity," *Semin Immunol* 13:291-302 (2001).
Guy, et al. "Expression of the neu protooncogene in the mammary epithelium of transgenic mice induces metastatic disease," *Proc. Natl. Acad. Sci. USA* 89:10578-10582 (1992).
Hollingsworth, et al., "Expression of MUC1, MUC2, MUC3, and MUC4 mucin mRNA in human pancreatic and intestinal tumor cell lines," *Int J Cancer* 57:198-203 (1994).
Hsu, et al. "Vaccination of patients with B-cell lymphoma using autologues antigenpulsed dendritic cells," *Nat Med.* 2:52-58 (1996).
Jeannon, et al. "Altered MUC1 and MUC2 glycoprotein expression in laryngeal cancer," *Otolaryngol Head Neck Surg.* 124:199-202 (2001).
Johnson, et al., "Characterization of a Nontoxic Monophosphoryl Lipid A," *Rev. Infect. Dis.* 9:S512 (1987).
Kaneda, "New Vector Innovation for Drug Delivery: Development of Fusigenic Non—Viral Particles," *Curr Drug Targets* 4(8):599-602 (2003).
Kim, et al., "Aberrant expression of MUC5AC and MUC6 gastric mucins and sialyl Tn antigen in intraepithelial neoplasms of the pancreas," *Gastroenterology* 123:1052-1060 (2002).
Kontani, et al., "Modulation of MUC1 mucin as an escape mechanism of breast cancer cells from autologous cytotoxic T-lymphocytes," *Br. J. Cancer* 84:1258-1264 (2001).
Kusuhara, et al., "Killing of naive T cells by C095L-transfected dendritic cells (DC): in vivo study using killer DC-DC hybrids and CD4+ T cells from DO11.10 mice," *Eur J Immunol* 32:1035-1043 (2002).
Luft, et al., "IFN—enhances CD40 ligand-mediated activation of immature monocyte-derived dendritic cells," *Int Immunol* 14:367-380 (2002).
Markowicz, et al., "Granulocyte-macrophage colony-stimulating factor promotes differentiation and survival of human peripheral blood dendritic cells in vitro," *J. Clin Invest.* 85:955-961 (1990).
Morein, et al., "Iscom, a novel structure for antigenic presentation of membrane proteins from enveloped viruses," *Nature* 308:457 (1984).
Muller, et al., "Single-step induction of mammary adenocarcinoma in transgenic mice bearing the activated c-neu oncogene," *Cell* 54(1):105-115 (1988).
Murphy, et al., "Infusion of dendritic cells pulsed with HLA-A2-specific prostate-specific membrane antigen peptides: a phase II prostate cancer vaccine trial involving patients with hormone-refractory metastatic disease," *Prostate* 38(1):73-78 (1999).
Nestle, et al. "Vaccination of melanoma patients with peptide- or tumor lysatepulsed dendritic cells," *Nat Med.* 4:328-332 (1998).
Nguyen, et al., "Membrane-bound (MUC1) and secretory (MUC2, MUC3, and MUC4) mucin gene expression in human lung cancer," *Tumor Biol.* 17(3):176-192 (1996).
O'Hagan, et al., "Biodegradable microparticles as controlled release antigen delivery systems," *Immunology* 73:239-242 (1991).
Paglia, et al., "Murine Dendritic Cells Loaded In Vitro with Soluble Protein Prime Cytotoxic T Lymphocytes against Tumor Antigen In Vivo," *J Exp Med* 183:317-322 (1996).
Redmond, et al., "Rotavirus particles function as immunological carriers for the delivery of peptides from infectious agents and endigenous proteins," *Mol. Immunol.* 28:269 (1991).
Regimbald, et al., "The breast mucin MUCI as a novel adhesion ligand for endothelial intercellular adhesion molecule 1 in breast cancer," *Cancer Res.* 56:4244-4249 (1996).
Ren, et al., "Protein Kinase C Regulates Function of the DF3/MUC1 Carcinoma Antigen in -Catenin Signaling," *J. Biol. Chem.* 277:17616-17622 (2002).
Retz, et al., "Differential mucin MUC7 gene expression in invasive bladder carcinoma in contrast to uniform MUC1 and MUC2 gene expression in both normal urothelium and bladder carcinoma," *Cancer Res* 58:5662-5666 (1998).
Rowse, et al., "Tolerance and immunity to MUC1 in a human MUC1 transgenic murine model," *Cancer Res.* 58:315 (1998).
Shortman, et al., "Dendritic Cell Development: Multiple Pathways to Nature's Adjuvants," *Stem Cells* 15:409-419 (1997).
Skov, et al., "IL-2 and IL-15 Regulate CD154 Expression on Activated CD4 T Cells1," *J Immunol.* 164: 3500-3505 (2000).
Steinbrink, et al., "CD4+ and CD8+ anergic T cells induced by interleukin-l0-treated human dendritic cells display antigen-specific suppressor activity," *Blood* 99:2468-2476 (2002).
Thomas, et al., "Non-viral gene therapy: polycation-mediated DNA delivery," *Appl Microbiol Biotechnol* 62(1):27-34(2003).
Wang, et al., "Essential roles of tumor-derived helper T cell epitopes for an effective peptide-based tumor vaccine," *Cancer Immun.* 3:16 (2003).
Xiang, et al., "A dual-function DNA vaccine encoding carcinoembryonic antigen and CD40 ligand trimer induces T cell-mediated protective immunity against colon cancer in carcinoembryonic antigen-transgenic mice," *The Journal of Immunology*, 167:4560-4565 (2001).
Yamamoto M., et al., "Interaction of the DF3/MUC1 Breast Carcinoma-associated Antigen and -Catenin in Cell Adhesion," *J. Biol. Chem.* 272:12492-12494 (1997).
Yanagi, et al., "Immuno-gene therapy with adenoviruses expressing fms-like tyrosine kinase 3 ligand and CD40 ligand for mouse hepatoma cells in vivo," *International Journal of Oncology* 22:345-351 (2003).
Yu, et al., "Overexpression of MUC5 genes is associated with early post-operativemetastasis in non-small-cell lung cancer," *Int. J. Cancer* 69:457-465 (1996).
Zhang, et al., "An adenoviral vector cancer vaccine that delivers a tumor-associated antigen/CD40-ligand fusion protein to dendritic cells," *Proc. Natl. Acad. Sci* (*USA*) 100(25)15101 (2003).
Zheng et al., "Induction of antitumor immunity via intratomoral tetra-costimulator protein transfer," *Cancer Research* 61:8127-8134 (2001).
Zitvogei, et al., "Therapy of murine tumors with tumor peptide-pulsed dendritic cells: dependence on T cells, B7 costimulation, and T helper cell 1-associated cytokines," *J Exp Med.* 183:87-97 (1996).
Zrihan-Licht S., et al., "Tyrosine phosphorylation of the MUC1 breast cancer membrane proteins. Cytokine receptor-like molecules," *FEBS Lett.* 356:130-136 (1994).
Tang et al., "Multistep process through which adenoviral vector vaccine overcomes anergy to tumor-associated antigens." *Blood*, 104:2704-2713, 2004.

Diehl et al., CD40 activation in vivo overcomes peptide-induced peripheral cytotoxic T-lymphocyte tolerance and arguments anti-tumor vaccine efficacy. Nature Medicine, 5(7): 774-779.
Scholl et al., Recombinant vaccinia virus encoding human MUCI ab IL2 as immunotherapy in patients with breast cancer. Journal of Immunotherapy, 23(5): 570-580, 2000.
Tang et al., Multistep process through which adenoviral vector vaccine overcomes anergy to tumor-associated antigens. Blood, 104(9), 2704-2713, 2004.
Tripp et al., CD40 ligand (CD154) enhances the Th1 and antibody responses to respiratory syncytical virun in the BALB/c mouse. The Journal of Immunology, 164: 5913-5921, 2000.
International Search Report for Application PCT/US04/39812.
Agrawal et al. "Cancer-associated MUC1 mucin Inhibits Human T-cell Proliferation, which is reversible by IL-2" Nature Medicine, 1998. 4(1): 43-49.
Koido et al. "Induction of Antitumor Immunity by Vaccination of Dendritic Cells Transfected with MUC1 RNA" J. Immunol., 2000. 165: 5713-5719.
Ren et al. "Human MUC1 Carcinoma-Associated Protein Confers Resistance to Genotoxic Anticancer Agents" Cancer Cell, 2004. 5: 163-175.
Akbulut et al. "Antitumor Immune Response Induced by I.T. Injection of Vector-Activated Dendritic Cells and Chemotherapy Suppresses Metastatic Breast Cancer" Mol Cancer Ther, 2006. 5(8):1975-1985.
Liu et al. "Tumor-Specific Therapeutic Effect Induced by an Oncolytic Adenoviral Vector Containing Heat Shock Protein 70 and Prodrug Activation Genes" Gene Therapy, 2006. 13:1235-1243.
Liu et al. "Tumor Vascular Targeting Therapy with Viral Vectors" Blood, 2006. 107(8): 3027-3033.
Lamikanra et al., "Regression of established human papillomavirus type 16 (HPV-16) immortalized tumors in vivo by vaccinia viruses expressing different forms of HPV-16 E7 correlates with enhanced CD8(+) T-cell responses that home to the tumor site," *J Virol* 75:9654-9664 (2001).
Liu et al., "Codon Modified Human Papillomavirus Type 16 E7 DNA Vaccine Enhances Cytotoxic T-lymphocyte Induction and Anti-tumor Activity" *Virology* 301:43-52 (2002).
Liu et al., "Adenovirus-mediated CD40 ligand gene-engineered dendritic cells elicit enhanced $CD8^+$cytotoxic T-cell activation and antitumor immunity," *Cancer Gene Therapy* 9:202-208 (2002).
Moingeon P., "Cancer vaccines," *Vaccine* 19(11-12):1305-1326 (2001).
Office communication for U.S. Appl. No. 11/009,533 dated Nov. 13, 2007.
Palucka and Banchereau, "Dendritic cells: A link between innate and adaptive immunity," *J Clin Immunol.* 19:12-25 (1999).
Timmerman and Levy, "Dendritic cell vaccines for cancer immunotherapy," *Annual Rev Med.* 50:507-529 (1999).
Xiang et al., "Protective immunity against human carcinoembryonic antigen (CEA) induced by an oral DNA vaccine in CEA-transgenic mice." *Clinical Cancer Research* 7(3 Suppl):856s-864s (2001).
Zwaveling et al., "Established human papillomavirus type 16-expressing tumors are effectively eradicated following vaccination with long peptides," *J Immunol*, 169:350-358 (2002).
Becker et al., Eradication of human hepatic and pulmonary melanoma metastases in SCID mice by antibody-interleukin 2 fusion proteins, Proc. Nat'l Academy of Sciences, Apr. 1996, vol. 93, pp. 2702-2707.
Xiang et al., Elimination of Established Murine Colon Carcinoma Metastases by Antibody-Interleukin 2 Fusion Protein Therapy, Cancer Research 57, pp. 4948-4955, Nov. 1, 1997.
Gillies et al., Antibody-IL-12 Fusion Proteins Are Effective in SCID Mouse, Models of Prostate and Colon Carcinoma Metastases, The Journal of Immunology, 1998, pp. 6195-6203, The American Association of Immunologists, Inc.
Schrama et al., Shift from Systemic to Site-Specific Memory by Tumor-Targeted IL-2, The Journal of Immunology, 2004, pp. 5843-5850, The American Association of Immunologists, Inc.

* cited by examiner

Fig. 1A

Human MUC-1 Encoding Nucleotide Sequence (SEQ ID NO: 1)

```
   1 ccgctccacc tctcaagcag ccagcgcctg cctgaatctg ttctgccccc tccccaccca
  61 tttcaccacc accatgacac cgggcaccca gtctcctttc ttcctgctgc tgctcctcac
 121 agtgcttaca gttgttacag gttctggtca tgcaagctct accccaggtg gagaaaagga
 181 gacttcggct acccagagaa gttcagtgcc cagctctact gagaagaatg ctgtgagtat
 241 gaccagcagc gtactctcca gccacagccc cggttcaggc tcctccacca ctcagggaca
 301 ggatgtcact ctggccccgg ccacggaacc agcttcaggt tcagctgcca cctggggaca
 361 ggatgtcacc tcggtcccag tcaccaggcc agccctgggc tccaccaccc cgccagccca
 421 cgatgtcacc tcagccccgg acaacaagcc agccccgggc tccaccgccc ccccagccca
 481 cggtgtcacc tcggccccgg acaccaggcc ggccccgggc tccaccgccc ccccagccca
 541 cggtgtcacc tcggccccgg acaccaggcc ggccccgggc tccaccgccc ccccagccca
 601 cggtgtcacc tcggccccgg acaccaggcc ggccccgggc tccaccgccc ccccagccca
 661 cggtgtcacc tcggccccgg acaccaggcc ggccccgggc tccaccgccc ccccagccca
 721 cggtgtcacc tcggccccgg acaccaggcc ggccccgggc tccaccgccc ccccagccca
 781 cggtgtcacc tcggccccgg acaccaggcc ggccccgggc tccaccgccc ccccagccca
 841 cggtgtcacc tcggccccgg acaccaggcc ggccccgggc tccaccgccc ccccagccca
 901 cggtgtcacc tcggccccgg acaccaggcc ggccccgggc tccaccgccc ccccagccca
 961 cggtgtcacc tcggccccgg acaccaggcc ggccccgggc tccaccgccc ccccagccca
1021 cggtgtcacc tcggccccgg acaccaggcc ggccccgggc tccaccgccc ccccagccca
1081 cggtgtcacc tcggccccgg acaccaggcc ggccccgggc tccaccgccc ccccagccca
1141 cggtgtcacc tcggccccgg acaccaggcc ggccccgggc tccaccgccc ccccagccca
1201 cggtgtcacc tcggccccgg acaccaggcc ggccccgggc tccaccgccc ccccagccca
1261 cggtgtcacc tcggccccgg acaccaggcc ggccccgggc tccaccgccc ccccagccca
1321 cggtgtcacc tcggccccgg acaccaggcc ggccccgggc tccaccgccc ccccagccca
1381 cggtgtcacc tcggccccgg acaccaggcc ggccccgggc tccaccgccc ccccagccca
1441 cggtgtcacc tcggccccgg acaccaggcc ggccccgggc tccaccgccc ccccagccca
1501 cggtgtcacc tcggccccgg acaccaggcc ggccccgggc tccaccgccc ccccagccca
1561 cggtgtcacc tcggccccgg acaccaggcc ggccccgggc tccaccgccc ccccagccca
1621 cggtgtcacc tcggccccgg acaccaggcc ggccccgggc tccaccgccc ccccagccca
1681 cggtgtcacc tcggccccgg acaccaggcc ggccccgggc tccaccgccc ccccagccca
1741 cggtgtcacc tcggccccgg acaccaggcc ggccccgggc tccaccgccc ccccagccca
1801 cggtgtcacc tcggccccgg acaccaggcc ggccccgggc tccaccgccc ccccagccca
1861 cggtgtcacc tcggccccgg acaccaggcc ggccccgggc tccaccgccc ccccagccca
1921 cggtgtcacc tcggccccgg acaccaggcc ggccccgggc tccaccgccc ccccagccca
1981 cggtgtcacc tcggccccgg acaccaggcc ggccccgggc tccaccgccc ccccagccca
2041 cggtgtcacc tcggccccgg acaccaggcc ggccccgggc tccaccgccc ccccagccca
2101 cggtgtcacc tcggccccgg acaccaggcc ggccccgggc tccaccgccc ccccagccca
2161 cggtgtcacc tcggccccgg acaccaggcc ggccccgggc tccaccgccc ccccagccca
2221 cggtgtcacc tcggccccgg acaccaggcc ggccccgggc tccaccgccc ccccagccca
2281 cggtgtcacc tcggccccgg acaccaggcc ggccccgggc tccaccgccc ccccagccca
2341 cggtgtcacc tcggccccgg acaccaggcc ggccccgggc tccaccgccc ccccagccca
2401 cggtgtcacc tcggccccgg acaccaggcc ggccccgggc tccaccgccc ccccagccca
2461 cggtgtcacc tcggccccgg acaccaggcc ggccccgggc tccaccgccc ccccagccca
2521 cggtgtcacc tcggccccgg acaccaggcc ggccccgggc tccaccgccc ccccagccca
2581 cggtgtcacc tcggccccgg acaccaggcc ggccccgggc tccaccgccc ccccagccca
2641 cggtgtcacc tcggccccgg acaccaggcc ggccccgggc tccaccgccc ccccagccca
2701 cggtgtcacc tcggccccgg acaccaggcc ggccccgggc tccaccgccc ccccagccca
2761 cggtgtcacc tcggccccgg acaccaggcc ggccccgggc tccaccgccc ccccagccca
2821 cggtgtcacc tcggccccgg acaccaggcc ggccccgggc tccaccgccc ccccagccca
2881 tggtgtcacc tcggccccgg acaacaggcc cgccttgggc tccaccgccc ctccagtcca
2941 caatgtcacc tcggcctcag gctctgcatc aggctcagct tctactctgg tgcacaacgg
3001 cacctctgcc agggctacca caacccccagc cagcaagagc actccattct caattcccag
```

Fig. 1B

```
3061 ccaccactct gatactccta ccacccttgc cagccatagc accaagactg atgccagtag
3121 cactcaccat agctcggtac ctcctctcac ctcctccaat cacagcactt ctccccagtt
3181 gtctactggg gtctctttct ttttcctgtc ttttcacatt tcaaacctcc agtttaattc
3241 ctctctggaa gatcccagca ccgactacta ccaagagctg cagagagaca tttctgaaat
3301 gtttttgcag atttataaac aagggggttt tctgggcctc tccaatatta agttcaggcc
3361 aggatctgtg gtggtacaat tgactctggc cttccgagaa ggtaccatca atgtccacga
3421 cgtggagaca cagttcaatc agtataaaac ggaagcagcc tctcgatata acctgacgat
3481 ctcagacgtc agcgtgagtg atgtgccatt tcctttctct gcccagtctg gggctggggt
3541 gccaggctgg ggcatcgcgc tgctggtgct ggtctgtgtt ctggttgcgc tggccattgt
3601 ctatctcatt gccttggctg tctgtcagtg ccgccgaaag aactacgggc agctggacat
3661 ctttccagcc cgggatacct accatcctat gagcgagtac cccacctacc acacccatgg
3721 gcgctatgtg cccccctagca gtaccgatcg tagcccctat gagaaggttt ctgcaggtaa
3781 cggtggcagc agcctctctt acacaaaccc agcagtggca gccgcttctg ccaacttgta
3841 gggcacgtcg ccgctgagct gagtggccag ccagtgccat tccactccac tcaggttctt
3901 caggccagag cccctgcacc ctgtttgggc tggtgagctg ggagttcagg tgggctgctc
3961 acagcctcct tcagaggccc caccaatttc tcggacactt ctcagtgtgt ggaagctcat
4021 gtgggcccct gaggctcatg cctgggaagt gttgtggggg ctcccaggag gactggccca
4081 gagagccctg agatagcggg gatcctgaac tggactgaat aaaacgtggt ctcccactg
```

FIG. 2

Human MUC-1 Amino Acid Sequence (SEQ ID NO: 2)

```
        1          11         21         31         41         51
   1 MTPGTQSPFF LLLLLTVLTV VTGSGHASST PGGEKETSAT QRSSVPSSTE KNAVSMTSSV    60
  61 LSSHSPGSGS STTQGQDVTL APATEPASGS AATWGQDVTS VPVTRPALGS TTPPAHDVTS   120
 121 APDNKPAPGS TAPPAHGVTS APDTRPAPGS TAPPAHGVTS APDTRPAPGS TAPPAHGVTS   180
 181 APDTRPAPGS TAPPAHGVTS APDTRPAPGS TAPPAHGVTS APDTRPAPGS TAPPAHGVTS   240
 241 APDTRPAPGS TAPPAHGVTS APDTRPAPGS TAPPAHGVTS APDTRPAPGS TAPPAHGVTS   300
 301 APDTRPAPGS TAPPAHGVTS APDTRPAPGS TAPPAHGVTS APDTRPAPGS TAPPAHGVTS   360
 361 APDTRPAPGS TAPPAHGVTS APDTRPAPGS TAPPAHGVTS APDTRPAPGS TAPPAHGVTS   420
 421 APDTRPAPGS TAPPAHGVTS APDTRPAPGS TAPPAHGVTS APDTRPAPGS TAPPAHGVTS   480
 481 APDTRPAPGS TAPPAHGVTS APDTRPAPGS TAPPAHGVTS APDTRPAPGS TAPPAHGVTS   540
 541 APDTRPAPGS TAPPAHGVTS APDTRPAPGS TAPPAHGVTS APDTRPAPGS TAPPAHGVTS   600
 601 APDTRPAPGS TAPPAHGVTS APDTRPAPGS TAPPAHGVTS APDTRPAPGS TAPPAHGVTS   660
 661 APDTRPAPGS TAPPAHGVTS APDTRPAPGS TAPPAHGVTS APDTRPAPGS TAPPAHGVTS   720
 721 APDTRPAPGS TAPPAHGVTS APDTRPAPGS TAPPAHGVTS APDTRPAPGS TAPPAHGVTS   780
 781 APDTRPAPGS TAPPAHGVTS APDTRPAPGS TAPPAHGVTS APDTRPAPGS TAPPAHGVTS   840
 841 APDTRPAPGS TAPPAHGVTS APDTRPAPGS TAPPAHGVTS APDTRPAPGS TAPPAHGVTS   900
 901 APDTRPAPGS TAPPAHGVTS APDTRPAPGS TAPPAHGVTS APDNRPALGS TAPPVHNVTS   960
 961 ASGSASGSAS TLVHNGTSAR ATTTPASKST PFSIPSHHSD TPTTLASHST KTDASSTHHS  1020
1021 SVPPLTSSNH STSPQLSTGV SFFFLSFHIS NLQFNSSLED PSTDYYQELQ RDISEMFLQI  1080
1081 YKQGGFLGLS NIKFRPGSVV VQLTLAFREG TINVHDVETQ FNQYKTEAAS RYNLTISDVS  1140
1141 VSDVPFPFSA QSGAGVPGWG IALLVLVCVL VALAIVYLIA LAVCQCRRKN YGQLDIFPAR  1200
1201 DTYHPMSEYP TYHTHGRYVP PSSTDRSPYE KVSAGNGGSS LSYTNPAVAA ASANL
```

MUCIN ANTIGEN VACCINE

CROSS-REFERENCE TO RELATED PATENT APPLICATIONS

This application is a claims priority to U.S. Provisional Patent Application No. 60/524,925, filed Nov. 24, 2003; and U.S. Provisional Patent Application No. 60/525,552, filed Nov. 25, 2003; and U.S. Provisional Patent Application No. 60/529,015, filed Dec. 11, 2003, from each of which priority is claimed, and each of which is hereby incorporated by reference in its entirety, including all tables, figures, and claims.

GOVERNMENTAL RIGHTS

This invention was made with Government support under Contract Number DAM017-99-1-9457 funded by the U.S. Army Medical Research and Material Command's funding agreement to the Sidney Kimmel Cancer Center. The Government has certain rights in this invention.

FIELD OF THE INVENTION

The present invention relates to the development of immunity against a mucin using a vector that expresses a secretable polypeptide comprising a mucin antigen fused to CD40 ligand.

BACKGROUND OF THE INVENTION

The following discussion of the background of the invention is merely provided to aid the reader in understanding the invention and is not admitted to describe or constitute prior art to the present invention. This application claims priority to U.S. application Ser. Nos. 60/524,925 (filed Nov. 24, 2003), 60/525,552 (filed Nov. 25, 2003), and 60/529,015 (filed Dec. 11, 2003), all of which are incorporated herein by reference in their entirety including the drawings. An application related to this application is PCT/US03/36237 filed Nov. 12, 2003 entitled "adenoviral vector vaccine," hereby incorporated by reference in its entirely including the drawings.

The activation of antigen presenting cells (APCs) which includes the dendritic cells (DCs), followed by loading of the antigen presenting cell with relevant antigens, is a requisite step in the generation of a T cell dependent immune response against cancer cells. Once activated and loaded with tumor antigens, DCs migrate to regional lymph nodes (LNs) to present antigens to T cells. Very commonly, these APCs express insufficient amounts of surface activation molecules which are required for optimal activation and expansion of T cell clones competent to recognize tumor antigens. See Shortman, et al., *Stem Cells* 15:409-419, 1997.

Antigen presentation to naive T cells, in the absence of costimulatory molecule expression on the surface of the APC, leads to anergy of the T cells. See Steinbrink, et al. *Blood* 99: 2468-2476, 2002. Moreover, cross-presentation by DCs without $CD4^+$ T cell help also results in peripheral deletion of Ag-specific T cells in regional LNs. See Kusuhara, et al., Eur J Immunol 32:1035-1043, 2002. In contrast, in the presence of $CD4^+$ T cell help, DCs acquire functional ability to cross-prime T cells, resulting in clonal expansion of effector T cells. See Gunzer, et al., Semin Immunol 13:291-302, 2001. This $CD4^+$ T cell help can be replaced with CD40-CD40 ligand (CD40L) interactions. See Luft, et al. Int Immunol 14:367-380, 2002. CD40L is a 33-kDa type II membrane protein and a member of the TNF gene family and is transiently expressed on $CD4^+$ T cells after TCR engagement. See Skov, et al. J Immunol. 164: 3500-3505, 2000.

The ability of DCs to generate anti-tumor immune responses in vivo has been documented in a number of animal tumor models. See Paglia, et al. J Exp Med 183: 317-322, 1996; Zitvogel, et al., J Exp Med. 183: 87-97, 1996. However, DC-mediated induction of immunity represents a major therapeutic challenge. It is considered difficult to ensure that the antigen presenting cells express appropriate adhesion molecules and chemokine receptors to attract DCs to secondary lymphoid organs for priming T cells. See Fong, et al. *J Immunol.* 166: 4254-4259, 2001; Markowicz, et al. *J Clin Invest.* 85: 955-961, 1990; Hsu, et al. *Nat Med.* 2: 52-58, 1996; Nestle, et al. *Nat Med.* 4: 328-332, 1998; Murphy, et al., *Prostate* 38: 73-78, 1999; Dhodapkar, et al. *J Clin Invest.* 104: 173-180, 1999.

SUMMARY OF THE INVENTION

In a first aspect, the invention provides an expression vector for generating immunity against a mucin. The vector includes a transcription unit encoding a secretable polypeptide that contains a secretory signal sequence, a mucin antigen and CD40 ligand. In a preferred embodiment, the the CD40 ligand is human CD40 ligand.

In one approach, the sequence encoding the mucin antigen in the transcription unit is 5' to sequence encoding the CD40 ligand. In another approach, the sequence encoding the CD40 ligand in the transcription unit is 5' to sequence encoding the mucin antigen. In a preferred embodiment, the CD40 ligand lacks all or a portion of its transmembrane domain.

In preferred embodiments, the expression vector may be a viral expression vector or a non-viral expression vector; e.g., an adenoviral vector; the mucin antigen is from a mucin selected from the group consisting of MUC1, MUC2, MUC3A, MUC3B, MUC4, MUC5AC, MUC5B, MUC6, MUC7, MUC8, MUC9, MUC12, MUC13, MUC15, and MUC16; the mucin antigen is from MUC1; the mucin antigen includes the extracellular domain of a mucin; or at least one tandem repeat of a mucin; and the transcription unit includes sequence that encodes a linker between the tumor antigen and the CD40 ligand. Suitable linkers may vary in length and composition.

In other embodiments, the expression vector includes a human cytomegalovirus promoter/enhancer for controlling transcription of the transcription unit.

In another aspect, the invention provides methods for generating an immune response in an individual against cells expressing a mucin antigen by administering an effective amount of a vector that includes a transcription unit encoding a polypeptide containing, starting from the amino terminus, a secretory signal sequence, the mucin antigen and a secretable form of CD40 ligand.

In preferred embodiments, the cells are cancer cells; and the method results in the generation of cytotoxic $CD8^+$ T cells against the mucin.

In yet another aspect, the invention provides methods for treating an individual with cancer that expresses a mucin antigen. The method includes administering to the individual an effective amount of a vector that has a transcription unit encoding a mucin antigen and CD40 ligand containing polypeptide as described above.

In preferred embodiments, the cancer cells are carcinoma cancer cells.

In a further aspect, the invention provides a method for generating an immune response to a mucin in a human where the mucin is a human self antigen and the immune cells of the individual are anergic to the mucin. The method includes administering to the individual an effective amount of a vector that has a transcription unit encoding a mucin antigen and CD40 ligand containing polypeptide as described above.

In the above methods, the vector is advantageously administered subcutaneously and may be given one or more subsequent times to increase the immune response. The immunity against the antigen is long lasting and involves generation of cytotoxic $CD8^+$ T cells.

Abbreviations used herein include "Ad" (adenoviral); "sig" (signal sequence); and "ecd" (extracellular domain).

These and other embodiments are described in detail below.

BRIEF DESCRIPTION OF THE DRAWINGS

FIGS. 1A and 1B show the nucleotide sequence encoding human MUC1 (SEQ ID NO:1)

FIG. 2 shows the amino acid sequence of human MUC1 (SEQ ID NO:2).

DETAILED DESCRIPTION OF THE INVENTION

In accordance with one aspect of the invention, a vector is provided for generating immunity against a mucin antigen. The vector includes a transcription unit encoding a secretable polypeptide containing a secretory signal sequence, a mucin antigen and CD40 ligand. In a preferred embodiment, the transcription unit includes from the amino terminus, a secretory signal sequence, a mucin antigen and a secretable form of CD40 ligand. In preferred embodiments, the secretable form of CD40 ligand lacks all or substantially all of its transmembrane domain.

The term "vector" which contains a transcription unit (aka. "expression vector") as used herein refers to viral and non-viral expression vectors that when administered in vivo can enter target cells and express an encoded protein. Viral vectors suitable for delivery in vivo and expression of an exogenous protein are well known and include adenoviral vectors, adeno-associated viral vectors, retroviral vectors, herpes simplex viral vectors, and the like. Viral vectors are preferably made replication defective in normal cells. See U.S. Pat. Nos. 6,669,942; 6,566,128; 6,794,188; 6,110, 744; 6,133,029.

The term "adenoviral expression vector" as used herein, refers to any vector from an adenovirus that includes exogenous DNA inserted into its genome which encodes a polypeptide. The vector must be capable of replicating and being packaged when any deficient essential genes are provided in trans. An adenoviral vector desirably contains at least a portion of each terminal repeat required to support the replication of the viral DNA, preferably at least about 90% of the full ITR sequence, and the DNA required to encapsidate the genome into a viral capsid. Many suitable adenoviral vectors have been described in the art. See U.S. Pat. Nos. 6,440,944 and 6,040,174 (replication defective E1 deleted vectors and specialized packaging cell lines). A preferred adenoviral expression vector is one that is replication defective in normal cells.

Adeno-associated viruses represent a class of small, single-stranded DNA viruses that can insert their genetic material at a specific site on chromosome 19. The preparation and use of adeno-associated viral vectors for gene delivery is described in U.S. Pat. No. 5,658,785.

Non-viral vectors for gene delivery comprise various types of expression vectors (e.g., plasmids) which are combined with lipids, proteins and other molecules (or combinations of thereof) in order to protect the DNA of the vector during delivery. Fusigenic non-viral particles can be constructed by combining viral fusion proteins with expression vectors as described. Kaneda, *Curr Drug Targets* (2003) 4(8):599-602. Reconstituted HVJ (hemagglutinating virus of Japan; Sendai virus)-liposomes can be used to deliver expression vectors or the vectors may be incorporated directly into inactivated HVJ particles without liposomes. See Kaneda, *Curr Drug Targets* (2003) 4(8):599-602. DMRIE/DOPE lipid mixture are useful a vehicle for non-viral expression vectors. See U.S. Pat. No. 6,147,055. Polycation-DNA complexes also may be used as a non-viral gene delivery vehicle. See Thomas et al., *Appl Microbiol Biotechnol* (2003) 62(1):27-34.

The term "transcription unit" as it is used herein in connection with an expression vector means a stretch of DNA that is transcribed as a single, continuous mRNA strand by RNA polymerase, and includes the signals for initiation and termination of transcription. For example, in one embodiment, a transcription unit of the invention includes nucleic acid that encodes from 5' to 3,' a secretory signal sequence, a mucin antigen and CD40 ligand. The transcription unit is in operable linkage with transcriptional and/or translational expression control elements such as a promoter and optionally any upstream or downstream enhancer element(s). A useful promoter/enhancer is the cytomegalovirus (CMV) immediate-early promoter/enhancer. See U.S. Pat. Nos. 5,849,522 and 6,218,140.

The term "secretory signal sequence" (aka. "signal sequence,""signal peptide," leader sequence," or leader peptide") as used herein refers to a short peptide sequence, generally hydrophobic in charter, including about 20 to 30 amino acids which is synthesized at the N-terminus of a polypeptide and directs the polypeptide to the endoplasmic reticulum. The secretory signal sequence is generally cleaved upon translocation of the polypeptide into the endoplasmic reticulum. Eukaryotic secretory signal sequences are preferred for directing secretion of the exogenous gene product of the expression vector. A variety of suitable such sequences are well known in the art and include the secretory signal sequence of human growth hormone, immunoglobulin kappa chain, and the like. In some embodiments the endogenous mucin signal sequence also may be used to direct secretion.

The term "tumor associated antigen" (TAA) as used herein refers to a protein which is present on tumor cells, and on normal cells during fetal life (onco-fetal antigen), after birth in selected organs, or on many normal cells, but at much lower concentration than on tumor cells. A variety of TAA have been described. An exemplary TAA is a mucin such as MUC1, described in further detail below. In contrast, tumor specific antigen (TSA) (aka. "tumor-specific transplantation antigen or TSTA) refers to a protein absent from normal cells. TSAs usually appear when an infecting virus has caused the cell to become immortal and to express a viral antigen(s). An exemplary viral TSA is the E6 or E7 proteins of HPV type 16. TSAs not induced by viruses include idiotypes the immunoglobulin idiotypes associated with B cell lymphomas or the T cell receptor (TCR) on T cell lymphomas. TAAs are more common than TSAs.

Both TAA and TSA may be the immunological target of an expression vector vaccine. Unless indicated otherwise, the term "tumor antigen" is used herein to refer collectively to TAA and TSA.

The term "mucin" as used herein refers to any of a class of high molecular weight glycoproteins with a high content of clustered oligosaccharides O-glycosidically linked to tandem repeating peptide sequences which are rich in threonine, serine and proline. Mucin plays a role in cellular protection and, with many sugars exposed on the extended structure, effects multiple interactions with various cell types including leukocytes and infectious agents. Mucin antigens also include those identified as CD227, Tumor-associated epithelial membrane antigen (EMA), Polymorphic epithelial mucin (PEM), Peanut- reactive urinary mucin (PUM), episialin, Breast carcinoma-associated antigen DF3, H23 antigen, mucin 1, Episialin, Tumor-associated mucin, Carcinoma- associated mucin. Also included are CA15-3 antigen, M344 antigen, Sialosyl Lewis Antigen (SLA), CA19-9, CA195 and other mucin antigen previously identified by monoclonal antibodies (e.g., see U.S. Pat. No. 5,849,876). The term mucin does not include proteoglycans which are glycoproteins characterized by glycosaminoglycan chains covalently attached to the protein backbone.

At least 15 different mucins have been described including MU1, MUC2, MUC3A, MUC3B, MUC4, MUC5AC, MUC5B, MUC6, MUC7, MUC8, MUC9, MUC12, MUC13, MUC15, and MUC16 (these may also be designated with a hyphen between "MUC" and the number). The nucleotide sequence and amino acid sequence of these mucins are known. The NCBI and Swiss Prot accession nos. for each of these mucins are as follows: MUC1 (NCBI NM002456, Swiss Prot P15941), MUC2, (NCBI NM002457, Swiss Prot Q02817) MUC3A (NCBI AF113616, Swiss Prot Q02505), MUC3B (NCBI AJ291390, Swiss Prot Q9H195), MUC4 (NCBI NM138299, Swiss Prot Q99102), MUC5AC (NCBI AF043909, Swiss Prot Q8WWQ5), MUC5B (Swiss Prot Q9HC84), MUC6 (NCBI U97698, Swiss Prot Q8N811), MUC7 (NCBI L42983, Swiss Prot Q8TAX7), MUC8 (NCBI U14383, Swiss Prot Q12964), MUC9 (NCBI U09550, Swiss Prot Q12889), MUC12 (Swiss Prot Q9UKN1), MUC13 (NCBI NM017648, Swiss Prot Q9H3R2), MUC15 (NCBI NM145650, Swiss Prot Q8WW41), and MUC16 (NCBI AF361486, Swiss Prot Q8WX17; aka CA125).

There are two structurally and functionally distinct classes of mucins: secreted gel-forming mucins (MUC2, MUC5AC, MUC5B, and MUC6) and transmembrane mucins (MUC1, MUC3A, MUC3B, MUC4, MUC12, MUC17). The products of some MUC genes do not fit well into either class (MUC7, MUC8, MUC9, MUC13, MUC15, MUC16).

The characteristics of particular mucins as TAA in particular cancers is supported by alterations in expression and structure in association with pre-neoplastic and neoplastic lesions (Filipe MI: Invest Cell Pathol 1979, 2:195-216; Filipe MI, Acta Med Port 1979, 1:351-365). For instance, normal mucosa of the stomach is characterized by the expression of MUC1, MUC5A/C, MUC6 mRNA and the encoded immunoreactive protein. Also, high levels of MUC2, MUC3 mucin mRNA and encoded immunoreactive protein are associated with intestinal metaplasia. Gastric cancer exhibits markedly altered secretory mucin mRNA levels compared with adjacent normal mucosa, with decreased levels of MUC5 and MUC6 mRNA and increased levels of MUC3 and MUC4 mRNA. High levels of MUC2 and MUC3 mRNA and protein are detectable in the small intestine, and MUC2 is the most abundant colonic mucin.

Mucins represent diagnostic markers for early detection of pancreatic cancer and other cell types. Studies have shown, that ductal adenocarcinomas (DACs) and tumor cell lines commonly overexpress MUCI mucin . See Andrianifahanana et al., Clin Cancer Res 2001, 7:4033-4040). This mucin was detected only at low levels in the most chronic pancreatitis and normal pancreas tissues but is overexpressed in all stages of pancreatic cancers. The de novo expression of MUC4 in pancreatic adenocarcinoma and cell lines has been reported (Hollingsworth et al., Int J Cancer 1994, 57:198-203). MUC4 mRNA expression has been observed in the majority of pancreatic adenocarcinoma and established pancreatic cancer cell lines but not in normal pancreas or chronic pancreatitis tissues. MUC4 expression also has been associated with lung cancer (see Nguyen et al. 1996 Tumor Biol. 17:176-192). MUC5 is associated with metastases in non-small cell lung cancer (see Yu et al., 1996 Int. J. Cancer 69:457-465). MUC6 is overexpressed and MUC5AC is de novo expressed in gastric and invasive DACs (Kim et al., Gastroenterology 2002, 123:1052-1060). MUC7 has been reported as a marker for invasive bladder cancer (see Retz et al. 1998 Cancer Res. 58:5662-5666)

Expression of the MUC2 secreted gel-forming mucin is generally decreased in colorectal adenocarcinoma, but preserved in mucinous carcinomas, a distinct subtype of colon cancer associated with microsatellite instability. MUC2 is increased in laryngeal cancer (Jeannon et al. 2001 Otolaryngol Head Neck Surg. 124:199-202). Another secreted gel-forming mucin, MUC5AC, a product of normal gastric mucosa, is absent from normal colon, but frequently present in colorectal adenomas and colon cancers.

MUC1, also known as episialin, polymorphic epithelial mucin (PEM), mucin like cancer associated antigen (MCA), CA27.29, peanut-reactive urinary mucin (PUM), tumor-associated epithelial mucin, epithelial membrane antigen (EMA), human milk fat globule (HMFG) antigen, MUC1/REP, MUC1/SEC, MUC1/Y, CD227, is the most well known of the mucins. The gene encoding MUCI maps to 1q21-q24. The MUC1 gene contains seven exons and produces several different alternatively spliced variants. The tandem repeat domain is highly O-glycosylated and alterations in glycosylation have been shown in epithelial cancer cells.

MUC1 mRNA is polymorphic in size. There are presently nine isoforms of MUC1 based on alternate splicing (isoform no.: NCBI accession no.; 1: ID P15941-1, 2: ID P15941-2, 3: ID P15941-3, 4: ID P15941-4, 5: P15941-5, 6: ID P15941-6, 7: ID P15941-7, 8: ID P15941-8, and 9: ID P15941-9).

MUC1 isoform 1 (aka. MUC1/REP) is a polymorphic, type I transmembrane protein containing: 1) a large extracellular domain, primarily consisting of a 20-amino acid (aa) repeat motif (a region known as Variable Number (30-100) of tandem repeats-VNTR); 2) a transmembrane domain; and 3) a 72-aa cytoplasmic tail. During biosynthesis, the MUC1/REP protein is modified to a large extent, and a considerable number of O-linked sugar moieties confer mucin-like characteristics on the mature protein. Soon after translation, MUC1/REP is cleaved into two products that form a tightly associated heterodimer complex composed of a large extracellular domain, linked noncovalently to a much smaller protein including the cytoplasmic and transmembrane domains. The extracellular domain can be shed from the cell. Using Swiss Prot P15941 as a reference (see FIGS. 1A and 1B), the extracellular domain (ecm) of MUC1 isoform 1 represents amino acids 24 to 1158, the transmembrane domain represents 1159-1181, and the cytoplasmic domain represents 1182-1255. The SEA domain represents is 1034-1151 and represents a C-terminal portion of what is referred to as the extracellular domain. The SEA domain of a mucin is generally a target for proteolytic cleavage, yielding two subunits, the smaller of which is associated with the cell membrane.

MUC1 isoform 5 (aka MUC1/SEC) is a form of MUC1 that is secreted by cells. It has an extracellular domain that is identical to that of isoform 1 (MUC1/REP), but lacks a transmembrane domain for anchoring the protein to a cell membrane. MUC1 isoform 7 (aka MUC1/Y) contains the cytoplasmic and transmembrane domains observed in isoforms 1 (MUC1/REP) and 5 (MUC1/SEC), but has an extracellular domain that is smaller than MUC1, lacking the repeat motif and its flanking region (see Baruch A. et al., 1999 Cancer Res. 59, 1552-1561). Isoform 7 behaves as a receptor and binds the secreted isoform 5. Binding induces phosphorylation of isoform 7 and alters cellular morphology and initiates cell signaling through second messenger proteins such as GRB2, (see Zrihan-Licht S. et al., 1995 FEBS Lett. 356, 130-136). It has been shown that β-catenin interacts with the cytoplasmic domain of MUC1 (Yamamoto M. et al., 1997 J. Biol. Chem. 272, 12492-12494).

MUC1 is expressed focally at low levels on normal epithelial cell surfaces. See 15. Greenlee, et al., *Cancer Statistics CA Cancer J.* 50, 7-33 (2000); Ren, et al., *J Biol. Chem.* 277, 17616-17622 (2002); Kontani, et al., *Br. J Cancer* 84, 1258-1264 (2001); Rowse, et al., *Cancer Res.* 58, 315 (1998). MUC1 is overexpressed in carcinomas of the breast, ovary, pancreas as well as other carcinomas (see also Gendler S. J. et al, 1990 J. Biol. Chem. 265, 15286-15293). A correlation is found between acquisition of additional copies of MUC1 gene and high mRNA levels (p <0.0001), revealing the genetic mechanism responsible for MUC1 gene overexpression, and supporting the role of MUC1 gene dosage in the pathogenesis of breast cancer (Bièche I. et al.,. 1997 Cancer Genet. Cytogenet. 98, 75-80). MUC1 mucin, as detected immunologically, is increased in expression in colon cancers, which correlates with a worse prognosis and in ovarian cancers.

High level expression of the MUC1 antigen plays a role in neoplastic epithelial mucosal cell development by disrupting the regulation of anchorage dependent growth (disrupting E-cadherin function), which leads to metastases. See Greenlee, et al., Cancer Statistics CA Cancer J. 50, 7-33 (2000); Ren, et al. J. Biol. Chem. 277, 17616-17622 (2002). Non-MHC-restricted cytotoxic T cell responses to MUC1 have been reported in patients with breast cancer. See Kontani et al., *Br. J. Cancer* 84, 1258-1264 (2001). Human MUC1 transgenic mice ("MUC1.Tg") have been reported to be unresponsive to stimulation with human MUC1 antigen. See Rowse, et al., *Cancer Res.* 58, 315 (1998). Human MUC1 transgenic mice are useful for evaluating the development of immunity to MUC1 as a self antigen.

MUC1 protein and mRNA have been found in the ER-positive MCF-7 and BT-474 cells as well as in the ER-negative MDA-MB-231 and SK-BR-3 BCC cells. The mRNA Transcript level was higher in ER+ than in ER− cell lines. MUC1 reacts with intracellular adhesion molecule-1 (ICAM-1). At least six tandem repeats of MUC1 are need (Regimbald et al., 1996 Cancer Res. 56,4244-4249). The tandem repeat peptide of MUC1 from T-47D BCC was found to be highly O-glycosylated with 4.8 glycosylated sites per repeat, which compares to 2.6 sites per repeat for the mucin from milk.

The term "mucin antigen" as used herein refers to the full length mucin all or a portion of the mucin that contains an epitope characterized in being able to elicit cellular immunity using a MUC-CD40L expression vector administered in vivo as described herein. A "mucin antigen" includes one or more epitopes from the extracellular domain of a mucin such as one or more of the tandem repeat motifs associated with the VNTR, or the SEA region. A mucin antigen may contain the entire extracellular domain. Also included within the meaning of "mucin antigen" are variations in the sequence including conservative amino acid changes and the like which do not alter the ability of the antigen to elicit an immune response that crossreacts with a native mucin sequence.

The VNTR consists of variable numbers of a tandemly repeated peptide sequences which differ in length (and composition) according to a genetic polymorphism and the nature of the mucin. The VNTR may also include 5' and 3' regions which contain degenerate tandem repeats. For example, in MUC1, the number of repeats varies from 21 to 125 in the northern European population. In the U.S. the most infrequent alleles contains 41 and 85 repeats, while more common alleles have 60-84 repeats. The MUC1 repeat has the general repeating peptide sequence PDTRPAPGSTAPPAHGVTSA (SEQ ID NO: 3). Underlying the MUC1 tandem repeat is a genetic sequence polymorphism at three positions shown bolded and underlined (positions 2, 3 and 13). The concerted replacement DT→ES (sequence variation 1) and the single replacements P→Q (sequence variation 2), P→A (sequence variation 3), and P→T (sequence variation 4) have been identified and vary with position in the domain (see Engelmann et al., 2001 J. Biol. Chem. 276:27764-27769). The most frequent replacement DT→ES occurs in up to 50% of the repeats. Table 1 shows some exemplary tandem repeat sequences.

TABLE 1

Mucin Tandem Repeat Sequences

| Mucin | Tandem Repeat (SEQ ID NO:) | Mucin source |
|---|---|---|
| MUC1 | PDTRPAPGSTAPPAHGVTSA (SEQ ID NO: 3) | Mammary |
| | PDNKPAPGSTAPPAHGVTSA (SEQ ID NO: 33) | Pancreatic |
| MUC2 | PTTTPPITTTTTVTPTPTPTGTQT (SEQ ID NO: 4) | Intestinal Tracheobronchial |
| MUC3 | HSTPSFTSSITTTETTS (SEQ ID NO: 5) | Intestinal Gall Bladder |
| MUC4 | TSSASTGHATPLPVTD (SEQ ID NO: 6) | Colon Tracheobronchial |
| MUC5AC | TTSTTSAP (SEQ ID NO: 7) | Gastric Tracheobronchial |
| MUC5B | SSTPGTAHTLTMLTTTATTPTATGSTATP (SEQ ID NO: 8) | Tracheobronchial Salivary |
| MUC7 | TTAAPPTPSATTPAPPSSSAPG (SEQ ID NO: 9) | Salivary |
| MUC8 | TSCPRPLQEGTPGSRAAHALSRRGHRVHELPTSSPGGDTGF (SEQ ID NO: 10) | Tracheobronchial |

Although a mucin antigen as used herein may comprise only a single tandem repeat sequence motif, it should be understood that the immune response will generally be stronger and more efficiently generated if the vector encodes multiple such repeats. The invention vector preferably encodes mucin tandem repeats from 2-4, more preferably from 5-9, even more preferably from 10-19, yet even more preferably from 20-29, still more preferably from 30-39, and still yet more preferably from 40-50. Tandem repeats greater than 50 are possible and may include the number of such repeats found in natural mucins.

A mucin antigen as this term is used herein also may encompass tandem repeats from different types of mucins. For example, an expression vector may encode tandem repeats from two different mucins, e.g., MUC1 and MUC2. Such a vector also may encode multiple forms of the SEA domain as well or a combination of tandem repeats and one or more SEA domains.

A secretable form of a mucin is one which lacks all or substantially all of its transmembrane domain. The transmembrane domain of a mucin, if present, is generally about 24 amino acids in length and functions to anchor the mucin or a fragment of the mucin in the cell membrane. A secretable form of MUC1 in which all of the transmembrane domain has been deleted is MUC1 missing residues 1159-1181. A mucin missing substantially all of the transmembrane is one where the domain comprises 6 residues or less of sequence at one end of the transmembrane domain, more preferably less than about 4 residues of sequence at one end of the transmembrane domain, even more preferably less than about 2 residues of sequence on one end of the transmembrane domain, and most preferably 1 residue or less on one end of the transmembrane domain. Thus, a mucin that lacks substantially all of the transmembrane domain rendering the mucin secretable is one that contains no more than six residues of sequence on one end of the transmembrane domain. In a preferred embodiment, the vaccine vector transcription unit encodes a secretable form of mucin lacking the entire transmembrane domain.

It should be understood that a mucin which lacks a functional transmembrane domain may still include all or a portion of the cytoplasmic domain and all or a portion of the SEA region, if present.

A source of DNA encoding the various mucins, and mucin antigens may be obtained from mucin expressing cell lines using a commercial cDNA synthesis kit and amplification using a suitable pair of PCR primers that can be designed from the published mucin DNA sequences. For example, MUC1 or MUC2 encoding nucleic acid may be obtained from CRL-1500 cells, available from the American Type Culture Collection. Mucin encoding DNA also may be obtained by amplification from RNA or cDNA obtained or prepared from human or other animal tissues. For DNA segments that are not that large, the DNA may be synthesized using an automated oligonucleotide synthesizer.

The term "linker" as used herein with respect to the transcription unit of the expression vector refers to one or more amino acid residues between the mucin antigen and CD40 ligand. The composition and length of the linker may be determined in accordance with methods well known in the art and may be tested for efficacy. See e.g. Arai et al., "Design of the linkers which effectively separate domains of a bifunctional fusion protein" Protein Engineering, Vol. 14, No. 8, 529-532, August 2001. The linker is generally from about 3 to about 15 amino acids long, more preferably about 5 to about 10 amino acids long, however, longer or shorter linkers may be used or the linker may be dispensed with entirely. Longer linkers may be up to about 50 amino acids, or up to about 100 amino acids. A short linker of less than 10 residues is preferred when the mucin antigen is N-terminal to the CD40 ligand.

The term "CD40 ligand" (CD40L) as used herein refers a full length or portion of the molecule known also as CD154 or TNF5. CD40L is a type II membrane polypeptide having a cytoplasmic domain at its N-terminus, a transmembrane region and then an extracellular domain at its C-terminus. Unless otherwise indicated, the full length CD40L is designated herein as "CD40L," "wt CD40L" or "wtTmCD40L." The form of CD40L in which the cytoplasmic domain has been deleted is designated herein as "ΔCtCD40L." The form of CD40L where the transmembrane domain has been deleted is designated herein as "ΔTmCD40L." The form of CD40L where both the cytoplasmic and transmembrane domains have been deleted is designated herein as "ΔCtΔTmCD40L." The nucleotide and amino acid sequence of CD40L from mouse and human is well known in the art and can be found, for example, in U.S. Pat. No. 5,962,406 (Armitage et al.). Also included within the meaning of "CD40 ligand" are variations in the sequence including conservative amino acid changes and the like which do not alter the ability of the ligand to elicit an immune response to a mucin in conjunction the fusion protein of the invention.

Murine CD40L (mCD40L) is 260 amino acids in length. The cytoplasmic (Ct) domain of mCD40L extends approximately from position 1-22, the transmembrane domain extends approximately from position 23-46, while the extracellular domain extends approximately from position 47-260.

Human CD40L (hCD40L) is 261 amino acids in length. The cytoplasmic domain of hCD40L extends approximately from position 1-22, the transmembrane domain extends approximately from position 23-46, while the extracellular domain extends approximately from position 47-261.

A secretable form of CD40 ligand is one which is missing all or substantially all of its transmembrane domain. The transmembrane domain of CD40L which contains about 24 amino acids in length, functions to anchor CD40 ligand in the cell membrane. CD40L from which all of the transmembrane domain has been deleted is CD40 ligand lacking residues 23-46. CD40 ligand missing substantially all of the transmembrane is one that retains 6 residues or less of sequence at one end of the transmembrane domain, more preferably less than about 4 residues of sequence at one end of the transmembrane domain, even more preferably less than about 2 residues of sequence on one end of the transmembrane domain, and most preferably 1 residue or less on one end of the transmembrane domain. Thus, a CD40L that lacks substantially all of the transmembrane domain rendering the CD40L secretable is one that retains no more than six residues of sequence on one end of the domain. Such as CD40L would contain, in addition to the extracellular domain and optionally the cytoplasmic domain, and no more than amino acids 41-46 or 23-28 located in the transmembrane domain of CD40L. In a preferred embodiment, the vaccine vector transcription unit encodes a secretable form of CD40 containing less than 10% of the transmembrane domain. More preferably, CD40L contains no transmembrane domain.

It should be understood that a CD40L which lacks a functional transmembrane domain may still include all or a portion of the cytoplasmic domain. Likewise, a CD40L which lacks a functional transmembrane domain may include all or a substantial portion of the extracellular domain.

As used herein, an expression vector of the present invention can be administered as a vaccine to induce immunity to a mucin. The vector may be formulated as appropriate with a suitable pharmaceutically acceptable carrier. Accordingly, the vectors may be used in the manufacture of a medicament or pharmaceutical composition. Expression vectors may be formulated as solutions or lyophilized powders for parenteral administration. Powders may be reconstituted by addition of a suitable diluent or other pharmaceutically acceptable carrier prior to use. Liquid formulations may be buffered, isotonic, aqueous solutions. Powders also may be sprayed in dry form. Examples of suitable diluents are normal isotonic saline solution, standard 5% dextrose in water, or buffered sodium or ammonium acetate solution. Such formulations are especially suitable for parenteral administration, but may also be used for oral administration or contained in a metered dose inhaler or nebulizer for insufflation. It may be desirable to add excipients such as polyvinylpyrrolidone, gelatin, hydroxy cellulose, acacia, polyethylene glycol, mannitol, sodium chloride, sodium citrate, and the like.

Alternately, vectors may be prepared for oral administration. Pharmaceutically acceptable solid or liquid carriers may be added to enhance or stabilize the composition, or to facilitate preparation of the vectors. Solid carriers include starch, lactose, calcium sulfate dihydrate, terra alba, magnesium stearate or stearic acid, talc, pectin, acacia, agar or gelatin. Liquid carriers include syrup, peanut oil, olive oil, saline and water. The carrier may also include a sustained release material such as glyceryl monostearate or glyceryl distearate, alone or with a wax. The amount of solid carrier varies but, preferably, will be between about 20 mg to about 1 g per dosage unit. When a liquid carrier is used, the preparation may be in the form of a syrup, elixir, emulsion, or an aqueous or non-aqueous suspension.

Vectors of the invention may be formulated to include other medically useful drugs or biological agents. The vectors also may be administered in conjunction with the administration of other drugs or biological agents useful for the disease or condition that the invention compounds are directed.

As employed herein, the phrase "an effective amount," refers to a dose sufficient to provide concentrations high enough to generate (or contribute to the generation of) an immune response in the recipient thereof. The specific effective dose level for any particular subject will depend upon a variety of factors including the disorder being treated, the severity of the disorder, the activity of the specific compound, the route of administration, the rate of clearance of the viral vectors, the duration of treatment, the drugs used in combination or coincident with the viral vectors, the age, body weight, sex, diet, and general health of the subject, and like factors well known in the medical arts and sciences. Various general considerations taken into account in determining the "therapeutically effective amount" are known to those of skill in the art and are described, e.g., in Gilman et al., eds., Goodman And Gilman's: The Pharmacological Bases of Therapeutics, 8th ed., Pergamon Press, 1990; and Remington's Pharmaceutical Sciences, 17th ed., Mack Publishing Co., Easton, Pa., 1990. For administration of vectors, the range of particles per administration typically if from about $1\times10^7$ to $1\times10^{11}$, more preferably $1\times10^8$ to $5\times10^{10}$, and even more preferably $5\times10^8$ to $2\times10^{10}$. A vector can be administered parenterally, such as intravascularly, intravenously, intraarterially, intramuscularly, subcutaneously, or the like. Administration can also be orally, nasally, rectally, transdermally or inhalationally via an aerosol. The vectors may be administered as a bolus, or slowly infused. Vector are preferably administered subcutaneously.

The invention recombinant expression vectors offer a potentially superior approach that allows a higher efficiency of gene transfer than that of DNA vaccines. As demonstrated herein, adenoviral vectors encoding tumor associated antigens can induce a protective cellular and humoral immunity against such antigens, including those to which tolerance had developed. Although not wishing to be bound by any theory, it is believed that the invention vaccines facilitated DCs maturation, promoting the development of effective antigen-specific immunity. It is also demonstrated herein that the secretable fusion protein encoding the extracellular domain of human MUC1 and the murine CD40L lacking a transmembrane and cytoplasmic domain (i.e. ecdhMUC1-ΔCtΔTmCD40L) produced from an adenoviral vector dramatically enhanced the potency of the cellular immune response to MUC1 expressing tumor cells. Although not wishing to be bound by any theory, it is believed that subcutaneous injection of the Ad-K-ecdhMUC1 -ΔCtΔTmCD40L vector elicited strong MUC1 specific CD8+ T cell-mediated immunity, which prevented the engraftment of cancer cells that expressed the MUC1 tumor associated antigen.

The immunity generated against the mucin antigen using the invention vector vaccine is long lasting. As used herein, the term "long lasting" means that immunity elicited to the mucin antigen encoded by the vector can be demonstrated for up to 6 months from the last administration, more preferably for up to 8 months, more preferably for up to one year, more preferably up to 1.5 years, and more preferably for at least two years.

In one embodiment, immunity to a mucin TAA can be generated by producing a fusion protein that comprises the extracellular domain of MUC1 fused to the amino-terminal end of the CD40 ligand from which the transmembrane and cytoplasmic domains were deleted. Construction of such vector is disclosed in the Examples. As was observed herein, subcutaneous administration of this adenoviral vector mucin vaccine induced a very robust and long lasting CD8+ cytotoxic T cell lymphocyte dependent systemic immune response against cancer cells which carry the MUC1 antigen. The mucin vaccine induced the production of memory cells, which underlie the long lasting immunity.

It was observed that vaccination of mice with the adenoviral vector Ad-sig-ecdhMUC1/ecdmCD40L induced an immune response which suppressed the growth of Human MUC1 (hMUC1) antigen positive tumor cells in 100% of mice transgenic for hMUC1 (i.e. these mice are anergic to the hMUC1 antigen prior to the vector injection. See Rowse, et al., *Cancer Res.* 58, 315 (1998). These results demonstrated that the Ad-sig-ecdhMUC1-ecd/ecdCD40L vector can be used for treating epithelial malignancies that express the MUC1.

Subcutaneous injection of the adenoviral MUC1 expression vector increased the level of hMUC1 specific T cells in the spleens of injected hMUC1 transgenic mice by 250 fold. The transgenic mice were anergic to the hMUC1 antigen prior to the vector injection. Thus, vector injection overcame the anergy, inducing a CD8+ T cell dependent systemic Th1 immune response that was antigen specific, and HLA restricted. The ability to overcome anergy as observed for vaccination with the adenoviral MUC1 expression vector was not observed when transgenic mice were vaccinated with purified ecdhMUC1/ecdCD40L-HIS protein.

Although not wishing to be bound by any theory, it is believed that the cells infected in the vicinity of the site of subcutaneous injection of the vector release the mucin antigen/CD40 ligand secretory which is taken up by antigen presenting cells (e.g. DCs) in the vicinity of the infected cells. The internalized mucin antigen would be digested in the proteosome with the resultant mucin antigen peptides trafficking to the endoplasmic reticulum where they would bind to Class I MHC molecules. Eventually, the DCs would present the mucin antigen on the surface in the Class I MHC molecule. Activated, tumor antigen-loaded antigen presenting cells would migrate to lymphocyte bearing secondary organs such as the regional lymph nodes or the spleen. During the two weeks of continuous release of the mucin antigen/CD40 ligand protein, CD8 cytotoxic T cell lymphocytes competent to recognize and kill cells which carried the tumor associated antigens would be expanded in the lymph nodes and spleen by the presence of the activated and antigen loaded dendritic cells. The continuous nature of the stimulation and the expansion of the mucin antigen specific cytotoxic T cells by the continuous release from the vector infected cells is believed to generate an immune response which would be greater in magnitude than is possible using a vector which carried a mucin antigen/CD40 ligand which is non-secretory.

The methods of the present invention, therefore, can be used to generate immunity to mucin which is a self-antigen in an individual. For example, a vector of the invention that encodes a mucin antigen from MUC1 can be used to generate $CD8^+$ immunity in a human where the MUC1 mucin antigen is a self antigen. The invention methods also can be used to overcome a state of immunological anergy to a mucin which is a self-antigen.

The following examples serve to illustrate the present invention. These examples are in no way intended to limit the scope of the invention.

EXAMPLES

1. Construction of Adenoviral Expression Vectors

The transcription unit, sig-ecdhMUC1-ΔCtΔTmCD40L of the adenoviral vector encodes a signal sequence (from an Ig kappa chain) followed by the extracellular domain of human MUC1 which is connected via a linker to a fragment of the CD40 ligand (human or mouse) which contains the extracellular domain without the transmembrane or cytoplasmic domains. The fusion protein was engineered to be secreted from vector infected cells by the addition of the kappa chain signal sequence to the amino-terminal end of the fusion protein.

The amino acid sequence of human MUC-1 and the encoding nucleotide sequence are shown in FIGS. 2 and 1A and 1B, respectively. The encoded MUC1 protein represents 1255 amino acids encoded by nucleotides 74 to 3,841 of SEQ ID NO: 1. The first 23 amino acids (encoded by 74 to 142 of SEQ ID NO:1) represent the MUC1 signal sequence which is removed from the mature mucin. The extracellular domain represents about 1135 amino acids from positions 24 to 1158 (encoded by nucleotides 143 to 3547). The tandem repeat region represents approximately 900 amino acids. Amino acids 74 to 126 (encoded by 229 to 451 of SEQ ID NO:1) represents a 5' degenerate tandem repeat region, amino acids 127 to 945 represents the tandem repeat region (encoded by 452 to 2,908 of SEQ ID NO: 1) while amino acids 946 to 962 represent a 3' degenerate tandem repeat region (encoded by 2809 to 2959 of SEQ ID NO:1). The SEA domain represents amino acids 1034 to 1151, the transmembrane domain represents 1159 to 1181, and the cytoplasmic domain represents 1182 to 1255 (see SEQ ID NO:2).

The transcription unit was introduced into the E1 gene region of the adenoviral vector backbone. After the adenoviral vector particles were generated in HEK 293 cells, the vector DNA was purified by cesium chloride gradient centrifugation. The presence of the signal peptide in the adenoviral vector was confirmed by restriction enzyme analysis and by DNA sequencing.

A transcription unit that included DNA encoding the signal sequence of the mouse IgG kappa chain gene upstream of DNA encoding human MUC-1 ("sig-ecdhMUC-1") was generated by PCR using plasmid pcDNA3-hMUC-1 (gift of Finn O.J., University of Pittsburgh School of Medicine) and the following primers: DNA encoding the mouse IgG kappa chain METDTLLLWVLLLWVPGSTGD (single letter amino acid code) (SEQ ID NO: 11) was prepared by PCR amplification (SEQ ID NOs: 12 ,13 and 14) to generate the full 21 amino acid mouse IgG kappa chain signal sequence (the start codon "ATG" is shown bolded in SEQ ID NO:12).

(SEQ ID NO: 12)
5'-CCACC ATG GAG ACA GAC ACA CTC CTG CTA TGG GTA CTG CTG-3'

(SEQ ID NO: 13)
5'-TC CTG CTA TGG GTA CTG CTG CTC TGG GTT CCA GGT TC-3'

-continued (SEQ ID NO: 14)
5'-TG CTC TGG GTT CCA GGT TCC ACT GGT GAG GAT G-3'

(SEQ ID NO: 15)
5'-GGT TCC ACT GGT GAC GAT GTC ACC TCG GTC CCA GTC-3' (forward primer for MUC-1 repeat region)

(SEQ ID NO: 16)
5'-GAGCTCGAG ATT GTG GAC TGG AGG GGC GGT G-3' (reverse primer for MUC-1 repeat region)

sig-ecdhMUC-1 with the upstream kappa signal sequence was generated by four rounds of PCR amplification (1$^{st}$ round: primers SEQ ID NOs 15 and 16, 2$^{nd}$ round: primer SEQ ID NOs 14 and 16; 3$^{rd}$ round: primer SEQ ID NOs 13 and 16; 4$^{th}$ round: primer SEQ ID NOs 12 and 16). The sig-ecdhMUC-1 encoding DNA was cloned into the pcDNA™ 3.1 TOPO vector (Invitrogen, San Diego, Calif.) forming pcDNA-sig-ecdhMUC-1.

pShuttle -ΔCtΔTmCD40L (no signal sequence and murine CD40L) was prepared as follows: Plasmid pDC406-mCD40L was purchased from the American Type Culture Collection. A pair of PCR primers (SEQ ID NOs: 17 and 18) was designed to amplify the mouse CD40 ligand from position 52 to 260 (i.e., without the cytoplasmic and transmembrane domains) and include sequence encoding a linker (indicated as "+ spacer") at the 5' end of the amplicon.

Mouse ΔCtΔTmCD40L+ spacer forward primer (MCD40LSPF) (CD40L sequence italicized; cloning site underlined and bolded):

(SEQ ID NO: 17)
5'-CCGCTCGAGAACGACGCACAAGCACCAAAATCAAAGGTCGAAG AGGAAGTA-3'.

Mouse CD40L reverse primer (MCD40LR; cloning site underlined)

(SEQ ID NO: 18)
5'-GCGGGCC CGCGGCCGCCGCTAG TCTAGA GAG TTT GAG TAA GCC AAA AGA TGA G-3'

The forward primer MCD40LSPF encodes a 10 residue spacer (LENDAQAPKS; single letter code; SEQ ID NO: 19) to be located between the mucin and the CD40 ligand (mCD40L) of the transcription unit. PCR performed using the forward and reverse primers (SEQ ID NOs 17 and 18) and plasmid pDC406-mCD40L as the template resulted in PCR fragment "space+ΔCtΔTMCD40L", which was inserted into the plasmid pcDNA-sig-ecdhMUC1 after restriction endonuclease digestion with XbaI (TCTAGA) and Xho I (CTCGAG). This vector is designated pcDNA-sig-ecdhMUC1/ΔCtΔTmCD40L. A vector was produced that was otherwise the same except that it encoded full length CD40L rather than the truncated form. This vector was made using a CD40 forward primer that annealed to the starting codons of murine CD40L. This vector is designated pShuttleCD40L (no signal sequence).

The sig-ecdhMUC1/ΔCtΔTmCD40L encoding DNA was cut from the pCDNA3TOPO vector using HindIII-XbaI restriction and inserted into pShuttle-CMV (see Murphy et al., *Prostate* 38: 73-78, 1999) downstream of the CMV promoter. The plasmid is designated pShuttle-sig-ecdhMUC1-ΔCtΔTmCD40L. Thus, the transcription unit sig-ecdh-MUC1-ΔCtΔTmCD40L encodes the mouse IgG kappa chain secretory signal followed by the extracellular domain of human MUC1 followed by a 10 amino acid linker with (NDAQAPK; residues 3-9 of SEQ ID NO: 19) followed by murine CD40 ligand residues 52-260.

In some vectors, the mouse HSF1 trimer domain was added between the ecdhMUC1 encoding DNA and ΔCtΔTm CD40L by PCR using plasmid pcDNA-sig-ecdhMUC1/ΔCtΔTmCD40L and the following primers:

```
                                    (SEQ ID NO: 20)
5'-AAC AAG CTC ATT CAG TTC CTG ATC TCA CTG GTG
GGATCC AAC GAC GCA CAA GCA CCA AAA TC-3'.

                                    (SEQ ID NO: 21)
5'- AGC CTT CGG CAG AAG CAT GCC CAG CAA CAG AAA
GTC GTC AAC AAG CTC ATT CAG TTC CTG-3'.

                                    (SEQ ID NO: 22)
5' AAT GAG GCT CTG TGG CGG GAG GTG GCC AGC CTT
CGG CAG AAG CAT G-3'.

                                    (SEQ ID NO: 23)
5'GAT ATC CTC AGG CTC GAG AAC GAC GCA CAA GCA CCA
AAA GAG AAT GAG GCT CTG TGG CGG G-3'.

                                    (SEQ ID NO: 18)
5'-GCGGGCC CGCGGCCGCCGCTAG TCTAGA GAG TTT GAG TAA
GCC AAA AGA TGA G-3'.
```

HSF1/ΔCtΔTm CD40L with the trimer domain sequence was generated by four rounds of PCR amplification (1st round: primers SEQ ID NOs 23 and 18; 2nd round: primer SEQ ID NOs 22 and 18; 3rd round: primer SEQ ID NOs 21 and 18; 4th round: primer SEQ ID NOs 20 and 18). The HSF1/ΔCtΔTm CD40L encoding DNA was cloned into pcDNA-sig-hMUC-1 restriction sites XbaI (TCTAGA) and Xho I (CTCGAG). The sequence between MUC1 and mCD40L is as follows:

LEN D A Q A P K ENEALWREVASFRQKHAQQQKV VNKLIQFLISLVG S N D A Q A P K S (SEQ ID NO: 24), wherein the underlined segment is the trimer sequence which is bonded by the linker LENDAQAPK (SEQ ID NO:25) and NDAQAPKS (SEQ ID NO:26).

In some vectors, a His tag encoding sequence was added to the end of the ΔCtΔTm CD40L and was generated by PCR using Plasmid pDC406-mCD40L (purchased from the American Type Culture Collection) and the following primers:

```
5'-CCG CTCGAG AACGACGCACAAGCACCAAAATCAAAGGTCGAA
GAGGAAGTA-3' (SEQ ID NO: 27) (forward primer)

5'-ATG GTG ATG ATG ACC GGT ACG GAG TTT GAG TAA GCC
AAA AGA TGA GAA GCC-3' (SEQ ID NO: 28)
(reverse primer)

5'-GTGC TCTAGA TCA GAATTC [ATG GTG ATG GTG ATG ATG]
ACC GGT ACG GAG-3' (SEQ ID NO: 29)
(poly His region encoded by nucleotides in the box)
```

Vector/ΔCtΔTm CD40L/His with the His tag sequence was generated by 2 rounds of PCR amplification (1st round: primers 1+2; 2nd round: primer 1+3). The /ΔCtΔTmCD40L/His encoding DNA was cloned into pcDNA-sig-ecdhMUC-1 restriction sites XbaI (TCTAGA) and Xho I (CTCGAG).

The recombinant adenoviral vectors were generated using the AdEasy vector system (Stratagene, San Diego, CA). Briefly the resulting piasmid pShuttie-sig-ecdhMUC1-ΔCtΔTmCD40L, and other control adenoviral vectors were linearized with Pme I and co-transformed into *E. coli* strain BJ5183 together with pAdEasy-1, the viral DNA plasmid. Recombinants were selected with kanamycin and screened by restriction enzyme analysis. The recombinant adenoviral construct was then cleaved with Pac I to expose its Inverted Terminal Repeats (ITR) and transfected into 293A cells to produce viral particles. The titer of recombinant adenovirus was determined by the Tissue culture Infectious Dose ($TCID_{50}$) method.

Primers for amplifying human ΔCtΔTmCD40L+ spacer using a human CD40 ligand cDNA template are set forth below.

Human ΔCtΔTmCD40L+ spacer forward primer (HCD40LSPF) (CD40L sequence italicized):

```
                                    (SEQ ID NO: 30)
5'-CCGCTCGAGAACGACGCACAAGCACCAAAATCAGTGTATCTT
CATAGAAGGTTGGACAAG-3'
```

Human CD40L reverse primer (HCD40LR)

```
                                    (SEQ ID NO: 31)
5'-CCCTCTAGA TCAGAGTTTGAGTAAGCCAAAGGAC-3'
```

These primers will amplify a ΔCtΔTmCD40L+ spacer which encodes 47-261 of human CD40L. The forward primer HCD40LSPF encodes a 10 residue spacer (LENDAQAPKS; single letter code; SEQ ID NO: 19) to be located between the tumor antigen and the CD40 ligand (hCD40L) of the transcription unit. PCR performed using the forward and reverse primers (SEQ ID NOs 30 and 31) and Plasmid pDC406-hCD40L as the template results in PCR fragment "space+ΔCtΔTmCD40L(human)," which is inserted into the plasmid pcDNA-sig-ecdhMUC1 after restriction endonuclease digestion with XbaI (TCTAGA) and Xho I (CTCGAG). The sig-ecdhMUC1/ΔCtΔTmCD40L (human) encoding DNA was cut from the pCDNA3TOPO using HindIII-XbaI restriction and inserted into pShuttle-CMV (see Murphy et al., *Prostate* 38: 73-78, 1999) downstream of the CMV promoter. This vector is designated pShuttle sig-ecdhMUC1/ΔCtΔTmCD40L(human). Modification of pShuttle sig-ecdh-MUC1/ΔCtΔTmCD40L(human) to include the ecdhMUC1 upstream of the human CD40 ligand sequence was accomplished essentially as described above for the murine CD40 ligand encoding vectors. Thus, the transcription unit sig-ecdhMUC1-ΔCtΔTmCD40L(human) encodes the kappa secretory signal followed by the extracellular domain of human MUC1 followed by a 10 amino acid linker (NDAQAPK; residues 3-9 of SEQ ID NO:19) followed by human CD40 ligand residues 47-261.

In an alternative approach, DNA encoding the human growth hormone signal sequence MATGSRTSLLLAF-GLLCLPWLQEGSA (single letter amino acid code) (SEQ ID NO: 32) could be used in place of the kappa chain signal sequence.

2. Overcoming Anergy to MUC1 in MUC1 Transgenic Mice a) Cytokine Production of Adenoviral Infected DCs Bone marrow derived DCs was harvested from hMUC-.Tg transgenic mice at 48 hours after exposure to the adenoviral vectors. The cells were exposed to vector at MOI 100, and plated in 24-well plates at $2\times10^5$ cells/ml. After incubation for 24 hours at 37° C., supernatant fluid (1 ml) was harvested and centrifuged to remove debris. The level of murine IL-12 or IFN-gamma released into the culture medium was assessed by enzyme-linked immunoadsorbent assay (ELISA) using the mouse IL- 12 p70 or IFN-gamma R & D Systems kits.

Bone marrow derived DCs contacted with the Ad-sig-ecdmMUC1-ΔCtΔTCD40L (murine) vector showed significantly increased the levels of interferon gamma and IL-12 cytokines from DCs harvested from the hMUC-.Tg transgenic mice at 48 hours after exposure to the vector. In contrast, virtually no cytokines were detected from restimulated DC's from animals immunized with an adenoviral vector that encoded the extracellular domain of hMUC1 but without fusion to a secretable form of CD40L. These results indicate that the ecdhMUOC1/ecdmCD40L (murine) fusion protein forms functional trimers and binds to the CD40 receptor on DCs.

b) Evaluation of Trimer Formation by ecdhMUC1-HSF1-ΔCtΔTmCD40L Fusion Protein Expressed from Ad-sig-ecdhMUC1-HSF1-ΔCtΔTmCD40L-HIS Trimerization of ecdhMUC1-HSF1-ΔCtΔTmCD40L-HIS fusion protein was evaluated following release from cells transformed with Ad-sig-ecdhMUC1-HSF1-ΔCtΔTmCD40L-HIS vector. The expressed fusion protein was purified from the supernatant of 293 cells exposed to the vector using a His Tag purification kit. Nondenaturing gel electrophoresis showed a molecular weight consistent with trimer. formation.

c) Effect of Ad-sig-ecdhMUC1-ΔCtΔTmCD40L Vector Injection on Establishment of MUC1 Expressing Cancer Cells.

hMUC1.Tg mice injected subcutaneously with the Ad-sig-ecdhMUC1-ΔCtΔTmCD40L (murine) vector were resistant to engraftment by the hMUC1 positive LL2/LL1hMUC1 mouse cancer cells. Control animals not injected with vector were not resistant to the growth of the same cells. Also, hMUC1.Tg mice injected with the Ad-sig-ecdhMUC1/ecdCD40L (murine) vector were not resistant to engraftment by parental cell line (LL2/LL1), which does not express MUC1.

hMUC1.Tg mice injected intravenously with ecdhMUC1-ΔCtΔTmCD40L (murine) protein were not resistant to engraftment by the hMUC1 positive LL2/LL1hMUC1 mouse cancer cells. Furthermore, hMUC1.Tg mice injected with Ad-sig-ecdhMUC1-ΔCtΔTmCD40L (murine) vector lived longer than did control vector injected mice subsequently administered the LL2/LL1hMUC1 cell line.

3. Cellular Mechanisms Underlying Breakdown of Anergy a) Cytokine Release from Vaccinated vs. Non Vaccinated Mice.

A population of splenic $CD8^+$ T lymphocytes was obtained seven days following Ad-sig-ecdhMUC1-ΔCtΔTmCD40L (murine) vector administration was obtained by depleting $CD4^+$ T lymphocytes using $CD4^+$ antibody coated magnetic beads. The isolated $CD8^+$ T lymphocytes released over 2,000 times the level of interferon gamma as did $CD8^+$ T cells from MUC1.Tg mice administered a control vector (without MUC1).

b) Cytotoxicity Assay

Splenic T cells collected from hMUC1.Tg mice 7 days following administration of Ad-sig-ecdhMUC1-ΔCtΔTmCD40L (murine) vector were cultured with hMUC1 antigen positive LL2/LL1hMUC1 cancer cells in vitro for 7 days. The stimulated splenic T cells were mixed in varying ratios with either the hMUC1 positive LL2/LL1hMUC1 cells or the hMUC1 negative LL2/LL1 cancer cells. The results showed that T cells from Ad-sig-ecdhMUC1-ΔCtΔTmCD40L (munine) vector vaccinated mice were cytotoxic only for the cancer cells expressing hMUC1.

c) Ad-sig-ecdhMUC1-ΔCtΔTmCD40L Vector Injection Overcomes Resistance to Expansion of hMUC1 Specific T Cells.

DCs obtained in vitro from bone marrow cells were exposed to the Ad-sig-ecdhMUC1-ΔCtΔTmCD40L (murine) vector for 48 hours. Splenic $CD8^+$ T cells, obtained from hMUC1.Tg transgenic mice 7 days following no vector injection or subcutaneous injection with the Ad-sig-ecdhMUC1-ΔCtΔTmCD40L (murine) vector, were mixed in a 1/1 ratio with the Ad-sig-ecdhMUC1/ecdCD40L (murine) vector-infected DCs. The ERK1/EK2 proteins, the endpoint of the Ras/MAPK signaling pathway, were phosphorylated in the CD8+ T cells isolated from Ad-sig-ecdhMUC1-ΔCtΔTmCD40L vector injected hMUC1.Tg transgenic mice following 45 minutes of in vitro exposure to Ad-sig-ecdh-MUC1-ΔCtΔTmCD40L (murine) vector infected DCs. In contrast no increase in phosphorylation of ERK1 and ERK2 proteins was seen in CD8 positive T cells from unvaccinated hMUC1.Tg mice. These results demonstrate that CD8 positive T cells from MUC1.Tg transgenic mice vaccinated with the Ad-sig-ecdMUC1-ΔCtΔTmCD40L (murine) vector were no longer anergic to MUC1.

4. Tumor Immunotherapy by Vaccination with Vector Encoding a MUC1-CD40L Fusion Protein For a tumor prevention protocol, animals were administered Ad-sig-ecdhMUC-1/ecdCD40L vector on day 1, 7 and 21. Three weeks later, the animals were administered LL2/LL1hMUC-1 tumor cells subcutaneously. Two weeks later, mice were administered intravenously 500,000 LL2/LL1hMUC-1 tumor cells via the tail vein. The size of the subcutaneous tumor nodules which developed, were measured by caliper at multiple time points to determine the effect of the various vaccine schedules on the growth of the LL2/LL1hMUC-1 cells as subcutaneous nodules. Lung metastases were measured by lung total weight following sacrifice.

Subcutaneous tumor measurements were made at various time points. Vector vaccinated mice completely suppressed the appearance of subcutaneous LL2/LL1hMUC-1 tumor. Vector vaccinated animals also effectively suppressed the growth of metastatic cancer nodules developing in the lungs.

A tumor treatment (post establishement) protocol was evaluated. In this schedule, subcutaneous tumor (500,000 of the LL2/LL1hMUC-1) was administered on day 1 and vaccinations were carried out at day 5. Vector was administered on days 5, 12 and 26. Tumor was administered i.v. on day 35 and tumor development (subcutaneous and lung) evaluated at day 49. Reduction in the size of the subcutaneous tumor and the extent of lung metastatic nodules was reduced in vector vaccinated animals.

All patents and publications mentioned in the specification are indicative of the levels of those of ordinary skill in the art to which the invention pertains. All patents and publications are herein incorporated by reference to the same extent as if each individual publication was specifically and individually indicated to be incorporated by reference.

The invention illustratively described herein suitably may be practiced in the absence of any element or elements, limitation or limitations which is not specifically disclosed herein. Thus, for example, in each instance herein any of the terms "comprising,""consisting essentially of" and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

Other embodiments are set forth within the following claims.

What is claimed is:

1. An expression vector for generating an immunity against a mucin antigen, said vector comprising a transcription unit, said transcription unit comprising a nucleic acid operably linked to a promoter, said transcription unit encoding a secretable polypeptide, said encoded polypeptide comprising from the amino terminus, a secretory signal sequence, the mucin antigen, and CD40 ligand, wherein (i) the mucin antigen and the CD40 ligand lack all or substantially all of their transmembrane domains; (ii) the mucin antigen is attached to the amino-terminus of the extracellular domain of said CD40 ligand; and (iii) said encoded polypeptide is configured to promote MHC Class I restricted cytotoxic T lymphocytes.

2. The expression vector of claim 1 wherein said mucin antigen is from a mucin selected from the group consisting of MUC1, MUC2, MUC3A, MUC3B, MUC4, MUC5AC, MUC5B, MUC6, MUC7, MUC8, MUC9, MUC12, MUC13, MUC15, and MUC16.

3. The expression vector of claim 1 wherein said mucin antigen is MUC1.

4. The expression vector of claim 1 wherein said encoded polypeptide is also configured to overcome anergy in an immune deficient individual.

5. The expression vector of claim 1 wherein said mucin antigen comprises at least one tandem repeat of a mucin.

6. The expression vector of claim 1 wherein said mucin antigen comprises all or a part of the SEA domain of a mucin.

7. The expression vector of claim 4 wherein said mucin-antigen is the extracellular domain of MUC1.

8. The expression vector of claim 1 wherein said transcription unit encodes a linker between said mucin antigen and said CD40 ligand.

9. The expression vector of claim 1 wherein said encoded polypeptide is also configured to prevent growth of cancerous tumor cells bearing said mucin antigen.

10. The expression vector of claim 1 wherein said expression vector is a viral vector.

11. The expression vector of claim 1 wherein said viral vector is an adenoviral vector.

12. The expression vector of claim 1 wherein said CD40 ligand is human CD40 ligand and said encoded polypeptide is configured to treat cancerous tumor cells bearing said mucin antigen existing in an individual prior to an administering of the expression vector.

13. The expression vector of claim 1 wherein said CD40 ligand lacks a cytoplasmic domain.

14. The expression vector of claim 1 wherein the CD40 ligand includes no more than six residues from either end of the transmembrane domain.

15. The expression vector of claim 1 wherein said CD40 ligand is a human CD40 ligand and comprises amino acids 47-261 of the extracellular domain of SEQ ID NO:12.

16. The expression vector of claim 1 wherein said vector is a viral vector and said viral vector is rendered non-replicating.

17. The expression vector of claim 1 wherein said mucin antigen comprises at least one or more tandem repeats from the VNTR region of the extracellular domain of MUC1.

18. The expression vector of claim 1 wherein said mucin antigen is a fragment of said mucin antigen which comprises an extracellular domain of MUC1.

19. The expression vector of claim 18 wherein said fragment of said mucin antigen comprises at least one tandem repeat of a mucin.

20. The expression vector of claim 18 wherein said fragment of said mucin antigen contains an amino acid sequence that is a tumor specific antigen.

21. A viral expression vector for generating an immunity against a mucin antigen, said vector comprising a transcription unit, said transcription unit comprising a nucleic acid operably linked to a promoter, said transcription unit encoding a secretable polypeptide, said encoded polypeptide comprising from the amino terminus, a secretory signal sequence, the mucin antigen, and CD40 ligand, wherein (i) the mucin antigen comprises a fragment thereof which lacks its transmembrane domain; (ii) the CD40 ligand lacks all or substantially all of its transmembrane domain; (iii) the mucin antigen is attached to the amino-terminus of the extracellular domain of said CD40 ligand; and (iv) said encoded polypeptide is capable of preventing growth of cancerous tumor cells bearing said mucin antigen and treating cancerous tumor cells bearing said mucin antigen.

22. The viral expression vector of claim 21 wherein said fragment of said mucin antigen comprises at least one or more tandem repeats from the VNTR region of the extracellular domain of MUC1.

23. The viral expression vector of claim 21 where said encoded polypeptide is further capable of overcoming anergy in an immune deficient individual.

24. The expression vector of claim 1 wherein said CD40 ligand is human CD40 ligand and wherein said expression vector is also configured to induce shrinkage of a tumor comprising cancerous tumor cells bearing said mucin antigen existing in an individual prior to a first of repeated administrations of the expression vector.

25. The viral expression vector of claim 21 wherein said viral expression vector is an adenoviral expression vector.

26. The viral expression vector of claim 21 wherein said mucin antigen is directly attached to the amino terminus of said CD40 ligand.

27. The viral expression vector of claim 21 wherein said encoded polypeptide is further capable to promote a lasting generation of cytotoxic CD8+ T cells against said mucin antigen for at least one year.

28. The expression vector of claim 1 wherein said encoded polypeptide is configured to treat metastatic tumor cells bearing said mucin antigen existing in an individual prior to administration of the expression vector.

29. The viral expression vector of claim 21 wherein said encoded polypeptide is further capable of treating cancerous tumor cells bearing said mucin antigen existing in an individual prior to an administration of the viral expression vector.

30. The expression vector of claim 1 wherein said encoded polypeptide is also configured to promote a lasting generation of cytotoxic CD8 + cells against said mucin antigen for at least one year.

* * * * *

SEQUENCE LISTING

<160> NUMBER OF SEQ ID NOS: 33

<210> SEQ ID NO 1
<211> LENGTH: 4139
<212> TYPE: DNA
<213> ORGANISM: Homo sapiens

<400> SEQUENCE: 1
ccgctccacc tctcaagcag ccagcgcctg cctgaatctg ttctgccccc tccccaccca 60
tttcaccacc accatgacac cgggcaccca gtctcctttc ttcctgctgc tgctcctcac 120
agtgcttaca gttgttacag gttctggtca tgcaagctct accccaggtg gagaaaagga 180
gacttcggct acccagagaa gttcagtgcc cagctctact gagaagaatg ctgtgagtat 240
gaccagcagc gtactctcca gccacagccc cggttcaggc tcctccacca ctcagggaca 300
ggatgtcact ctggccccgg ccacggaacc agcttcaggt tcagctgcca cctggggaca 360
ggatgtcacc tcggtcccag tcaccaggcc agccctgggc tccaccaccc cgccagccca 420
cgatgtcacc tcagccccgg acaacaagcc agccccgggc tccaccgccc ccccagccca 480
cggtgtcacc tcggccccgg acaccaggcc ggccccgggc tccaccgccc ccccagccca 540
cggtgtcacc tcggccccgg acaccaggcc ggccccgggc tccaccgccc ccccagccca 600
cggtgtcacc tcggccccgg acaccaggcc ggccccgggc tccaccgccc ccccagccca 660
cggtgtcacc tcggccccgg acaccaggcc ggccccgggc tccaccgccc ccccagccca 720
cggtgtcacc tcggccccgg acaccaggcc ggccccgggc tccaccgccc ccccagccca 780
cggtgtcacc tcggccccgg acaccaggcc ggccccgggc tccaccgccc ccccagccca 840
cggtgtcacc tcggccccgg acaccaggcc ggccccgggc tccaccgccc ccccagccca 900
cggtgtcacc tcggccccgg acaccaggcc ggccccgggc tccaccgccc ccccagccca 960
cggtgtcacc tcggccccgg acaccaggcc ggccccgggc tccaccgccc ccccagccca 1020
cggtgtcacc tcggccccgg acaccaggcc ggccccgggc tccaccgccc ccccagccca 1080
cggtgtcacc tcggccccgg acaccaggcc ggccccgggc tccaccgccc ccccagccca 1140
cggtgtcacc tcggccccgg acaccaggcc ggccccgggc tccaccgccc ccccagccca 1200
cggtgtcacc tcggccccgg acaccaggcc ggccccgggc tccaccgccc ccccagccca 1260
cggtgtcacc tcggccccgg acaccaggcc ggccccgggc tccaccgccc ccccagccca 1320
cggtgtcacc tcggccccgg acaccaggcc ggccccgggc tccaccgccc ccccagccca 1380
cggtgtcacc tcggccccgg acaccaggcc ggccccgggc tccaccgccc ccccagccca 1440
cggtgtcacc tcggccccgg acaccaggcc ggccccgggc tccaccgccc ccccagccca 1500
cggtgtcacc tcggccccgg acaccaggcc ggccccgggc tccaccgccc ccccagccca 1560
cggtgtcacc tcggccccgg acaccaggcc ggccccgggc tccaccgccc ccccagccca 1620
cggtgtcacc tcggccccgg acaccaggcc ggccccgggc tccaccgccc ccccagccca 1680
cggtgtcacc tcggccccgg acaccaggcc ggccccgggc tccaccgccc ccccagccca 1740
cggtgtcacc tcggccccgg acaccaggcc ggccccgggc tccaccgccc ccccagccca 1800
cggtgtcacc tcggccccgg acaccaggcc ggccccgggc tccaccgccc ccccagccca 1860
cggtgtcacc tcggccccgg acaccaggcc ggccccgggc tccaccgccc ccccagccca 1920
cggtgtcacc tcggccccgg acaccaggcc ggccccgggc tccaccgccc ccccagccca 1980
cggtgtcacc tcggccccgg acaccaggcc ggccccgggc tccaccgccc ccccagccca 2040

```
cggtgtcacc tcggccccgg acaccaggcc ggccccgggc tccaccgccc ccccagccca   2100

cggtgtcacc tcggccccgg acaccaggcc ggccccgggc tccaccgccc ccccagccca   2160

cggtgtcacc tcggccccgg acaccaggcc ggccccgggc tccaccgccc ccccagccca   2220

cggtgtcacc tcggccccgg acaccaggcc ggccccgggc tccaccgccc ccccagccca   2280

cggtgtcacc tcggccccgg acaccaggcc ggccccgggc tccaccgccc ccccagccca   2340

cggtgtcacc tcggccccgg acaccaggcc ggccccgggc tccaccgccc ccccagccca   2400

cggtgtcacc tcggccccgg acaccaggcc ggccccgggc tccaccgccc ccccagccca   2460

cggtgtcacc tcggccccgg acaccaggcc ggccccgggc tccaccgccc ccccagccca   2520

cggtgtcacc tcggccccgg acaccaggcc ggccccgggc tccaccgccc ccccagccca   2580

cggtgtcacc tcggccccgg acaccaggcc ggccccgggc tccaccgccc ccccagccca   2640

cggtgtcacc tcggccccgg acaccaggcc ggccccgggc tccaccgccc ccccagccca   2700

cggtgtcacc tcggccccgg acaccaggcc ggccccgggc tccaccgccc ccccagccca   2760

cggtgtcacc tcggccccgg acaccaggcc ggccccgggc tccaccgccc ccccagccca   2820

cggtgtcacc tcggccccgg acaccaggcc ggccccgggc tccaccgccc ccccagccca   2880

tggtgtcacc tcggccccgg acaacaggcc cgccttgggc tccaccgccc ctccagtcca   2940

caatgtcacc tcggcctcag gctctgcatc aggctcagct tctactctgg tgcacaacgg   3000

cacctctgcc agggctacca caaccccagc cagcaagagc actccattct caattcccag   3060

ccaccactct gatactccta ccacccttgc cagccatagc accaagactg atgccagtag   3120

cactcaccat agctcggtac ctcctctcac ctcctccaat cacagcactt ctccccagtt   3180

gtctactggg gtctctttct tttcctgtc ttttcacatt tcaaacctcc agtttaattc    3240

ctctctggaa gatcccagca ccgactacta ccaagagctg cagagagaca tttctgaaat   3300

gtttttgcag atttataaac aagggggttt tctgggcctc tccaatatta agttcaggcc   3360

aggatctgtg gtggtacaat tgactctggc cttccgagaa ggtaccatca atgtccacga   3420

cgtggagaca cagttcaatc agtataaaac ggaagcagcc tctcgatata acctgacgat   3480

ctcagacgtc agcgtgagtg atgtgccatt tcctttctct gcccagtctg gggctggggt   3540

gccaggctgg ggcatcgcgc tgctggtgct ggtctgtgtt ctggttgcgc tggccattgt   3600

ctatctcatt gccttggctg tctgtcagtg ccgccgaaag aactacgggc agctggacat   3660

ctttccagcc cgggatacct accatcctat gagcgagtac cccacctacc acacccatgg   3720

gcgctatgtg ccccctagca gtaccgatcg tagcccctat gagaaggttt ctgcaggtaa   3780

cggtggcagc agcctctctt acacaaaccc agcagtggca gccgcttctg ccaacttgta   3840

gggcacgtcg ccgctgagct gagtggccag ccagtgccat tccactccac tcaggttctt   3900

caggccagag cccctgcacc ctgtttgggc tggtgagctg ggagttcagg tgggctgctc   3960

acagcctcct tcagaggccc caccaatttc tcggacactt ctcagtgtgt ggaagctcat   4020

gtgggcccct gaggctcatg cctgggaagt gttgtggggg ctcccaggag gactggccca   4080

gagagccctg agatagcggg gatcctgaac tggactgaat aaaacgtggt ctcccactg    4139
```

<210> SEQ ID NO 2
<211> LENGTH: 1255
<212> TYPE: PRT
<213> ORGANISM: Homo sapiens

<400> SEQUENCE: 2

```
Met Thr Pro Gly Thr Gln Ser Pro Phe Phe Leu Leu Leu Leu Leu Thr
  1               5                  10                  15
```

```
Val Leu Thr Val Val Thr Gly Ser Gly His Ala Ser Ser Thr Pro Gly
            20                  25                  30

Gly Glu Lys Glu Thr Ser Ala Thr Gln Arg Ser Ser Val Pro Ser Ser
        35                  40                  45

Thr Glu Lys Asn Ala Val Ser Met Thr Ser Ser Val Leu Ser Ser His
    50                  55                  60

Ser Pro Gly Ser Gly Ser Ser Thr Thr Gln Gly Gln Asp Val Thr Leu
65                  70                  75                  80

Ala Pro Ala Thr Glu Pro Ala Ser Gly Ser Ala Ala Thr Trp Gly Gln
                85                  90                  95

Asp Val Thr Ser Val Pro Val Thr Arg Pro Ala Leu Gly Ser Thr Thr
            100                 105                 110

Pro Pro Ala His Asp Val Thr Ser Ala Pro Asp Asn Lys Pro Ala Pro
        115                 120                 125

Gly Ser Thr Ala Pro Pro Ala His Gly Val Thr Ser Ala Pro Asp Thr
    130                 135                 140

Arg Pro Ala Pro Gly Ser Thr Ala Pro Pro Ala His Gly Val Thr Ser
145                 150                 155                 160

Ala Pro Asp Thr Arg Pro Ala Pro Gly Ser Thr Ala Pro Pro Ala His
                165                 170                 175

Gly Val Thr Ser Ala Pro Asp Thr Arg Pro Ala Pro Gly Ser Thr Ala
            180                 185                 190

Pro Pro Ala His Gly Val Thr Ser Ala Pro Asp Thr Arg Pro Ala Pro
        195                 200                 205

Gly Ser Thr Ala Pro Pro Ala His Gly Val Thr Ser Ala Pro Asp Thr
    210                 215                 220

Arg Pro Ala Pro Gly Ser Thr Ala Pro Pro Ala His Gly Val Thr Ser
225                 230                 235                 240

Ala Pro Asp Thr Arg Pro Ala Pro Gly Ser Thr Ala Pro Pro Ala His
                245                 250                 255

Gly Val Thr Ser Ala Pro Asp Thr Arg Pro Ala Pro Gly Ser Thr Ala
            260                 265                 270

Pro Pro Ala His Gly Val Thr Ser Ala Pro Asp Thr Arg Pro Ala Pro
        275                 280                 285

Gly Ser Thr Ala Pro Pro Ala His Gly Val Thr Ser Ala Pro Asp Thr
    290                 295                 300

Arg Pro Ala Pro Gly Ser Thr Ala Pro Pro Ala His Gly Val Thr Ser
305                 310                 315                 320

Ala Pro Asp Thr Arg Pro Ala Pro Gly Ser Thr Ala Pro Pro Ala His
                325                 330                 335

Gly Val Thr Ser Ala Pro Asp Thr Arg Pro Ala Pro Gly Ser Thr Ala
            340                 345                 350

Pro Pro Ala His Gly Val Thr Ser Ala Pro Asp Thr Arg Pro Ala Pro
        355                 360                 365

Gly Ser Thr Ala Pro Pro Ala His Gly Val Thr Ser Ala Pro Asp Thr
    370                 375                 380

Arg Pro Ala Pro Gly Ser Thr Ala Pro Pro Ala His Gly Val Thr Ser
385                 390                 395                 400

Ala Pro Asp Thr Arg Pro Ala Pro Gly Ser Thr Ala Pro Pro Ala His
                405                 410                 415

Gly Val Thr Ser Ala Pro Asp Thr Arg Pro Ala Pro Gly Ser Thr Ala
            420                 425                 430

Pro Pro Ala His Gly Val Thr Ser Ala Pro Asp Thr Arg Pro Ala Pro
```

```
        435                 440                 445

Gly Ser Thr Ala Pro Pro Ala His Gly Val Thr Ser Ala Pro Asp Thr
    450                 455                 460

Arg Pro Ala Pro Gly Ser Thr Ala Pro Pro Ala His Gly Val Thr Ser
465                 470                 475                 480

Ala Pro Asp Thr Arg Pro Ala Pro Gly Ser Thr Ala Pro Pro Ala His
                485                 490                 495

Gly Val Thr Ser Ala Pro Asp Thr Arg Pro Ala Pro Gly Ser Thr Ala
            500                 505                 510

Pro Pro Ala His Gly Val Thr Ser Ala Pro Asp Thr Arg Pro Ala Pro
        515                 520                 525

Gly Ser Thr Ala Pro Pro Ala His Gly Val Thr Ser Ala Pro Asp Thr
    530                 535                 540

Arg Pro Ala Pro Gly Ser Thr Ala Pro Pro Ala His Gly Val Thr Ser
545                 550                 555                 560

Ala Pro Asp Thr Arg Pro Ala Pro Gly Ser Thr Ala Pro Pro Ala His
                565                 570                 575

Gly Val Thr Ser Ala Pro Asp Thr Arg Pro Ala Pro Gly Ser Thr Ala
            580                 585                 590

Pro Pro Ala His Gly Val Thr Ser Ala Pro Asp Thr Arg Pro Ala Pro
        595                 600                 605

Gly Ser Thr Ala Pro Pro Ala His Gly Val Thr Ser Ala Pro Asp Thr
    610                 615                 620

Arg Pro Ala Pro Gly Ser Thr Ala Pro Pro Ala His Gly Val Thr Ser
625                 630                 635                 640

Ala Pro Asp Thr Arg Pro Ala Pro Gly Ser Thr Ala Pro Pro Ala His
                645                 650                 655

Gly Val Thr Ser Ala Pro Asp Thr Arg Pro Ala Pro Gly Ser Thr Ala
            660                 665                 670

Pro Pro Ala His Gly Val Thr Ser Ala Pro Asp Thr Arg Pro Ala Pro
        675                 680                 685

Gly Ser Thr Ala Pro Pro Ala His Gly Val Thr Ser Ala Pro Asp Thr
    690                 695                 700

Arg Pro Ala Pro Gly Ser Thr Ala Pro Pro Ala His Gly Val Thr Ser
705                 710                 715                 720

Ala Pro Asp Thr Arg Pro Ala Pro Gly Ser Thr Ala Pro Pro Ala His
                725                 730                 735

Gly Val Thr Ser Ala Pro Asp Thr Arg Pro Ala Pro Gly Ser Thr Ala
            740                 745                 750

Pro Pro Ala His Gly Val Thr Ser Ala Pro Asp Thr Arg Pro Ala Pro
        755                 760                 765

Gly Ser Thr Ala Pro Pro Ala His Gly Val Thr Ser Ala Pro Asp Thr
    770                 775                 780

Arg Pro Ala Pro Gly Ser Thr Ala Pro Pro Ala His Gly Val Thr Ser
785                 790                 795                 800

Ala Pro Asp Thr Arg Pro Ala Pro Gly Ser Thr Ala Pro Pro Ala His
                805                 810                 815

Gly Val Thr Ser Ala Pro Asp Thr Arg Pro Ala Pro Gly Ser Thr Ala
            820                 825                 830

Pro Pro Ala His Gly Val Thr Ser Ala Pro Asp Thr Arg Pro Ala Pro
        835                 840                 845

Gly Ser Thr Ala Pro Pro Ala His Gly Val Thr Ser Ala Pro Asp Thr
    850                 855                 860
```

```
Arg Pro Ala Pro Gly Ser Thr Ala Pro Pro Ala His Gly Val Thr Ser
865                 870                 875                 880

Ala Pro Asp Thr Arg Pro Ala Pro Gly Ser Thr Ala Pro Pro Ala His
                885                 890                 895

Gly Val Thr Ser Ala Pro Asp Thr Arg Pro Ala Pro Gly Ser Thr Ala
            900                 905                 910

Pro Pro Ala His Gly Val Thr Ser Ala Pro Asp Thr Arg Pro Ala Pro
        915                 920                 925

Gly Ser Thr Ala Pro Pro Ala His Gly Val Thr Ser Ala Pro Asp Asn
    930                 935                 940

Arg Pro Ala Leu Gly Ser Thr Ala Pro Pro Val His Asn Val Thr Ser
945                 950                 955                 960

Ala Ser Gly Ser Ala Ser Gly Ser Ala Ser Thr Leu Val His Asn Gly
                965                 970                 975

Thr Ser Ala Arg Ala Thr Thr Thr Pro Ala Ser Lys Ser Thr Pro Phe
            980                 985                 990

Ser Ile Pro Ser His His Ser Asp Thr Pro Thr Thr Leu Ala Ser His
        995                 1000                1005

Ser Thr Lys Thr Asp Ala Ser Ser Thr His His Ser Ser Val Pro Pro
   1010                1015                1020

Leu Thr Ser Ser Asn His Ser Thr Ser Pro Gln Leu Ser Thr Gly Val
1025                1030                1035                1040

Ser Phe Phe Phe Leu Ser Phe His Ile Ser Asn Leu Gln Phe Asn Ser
               1045                1050                1055

Ser Leu Glu Asp Pro Ser Thr Asp Tyr Tyr Gln Glu Leu Gln Arg Asp
           1060                1065                1070

Ile Ser Glu Met Phe Leu Gln Ile Tyr Lys Gln Gly Gly Phe Leu Gly
       1075                1080                1085

Leu Ser Asn Ile Lys Phe Arg Pro Gly Ser Val Val Val Gln Leu Thr
   1090                1095                1100

Leu Ala Phe Arg Glu Gly Thr Ile Asn Val His Asp Val Glu Thr Gln
1105                1110                1115                1120

Phe Asn Gln Tyr Lys Thr Glu Ala Ala Ser Arg Tyr Asn Leu Thr Ile
               1125                1130                1135

Ser Asp Val Ser Val Ser Asp Val Pro Phe Pro Phe Ser Ala Gln Ser
           1140                1145                1150

Gly Ala Gly Val Pro Gly Trp Gly Ile Ala Leu Leu Val Leu Val Cys
       1155                1160                1165

Val Leu Val Ala Leu Ala Ile Val Tyr Leu Ile Ala Leu Ala Val Cys
   1170                1175                1180

Gln Cys Arg Arg Lys Asn Tyr Gly Gln Leu Asp Ile Phe Pro Ala Arg
1185                1190                1195                1200

Asp Thr Tyr His Pro Met Ser Glu Tyr Pro Thr Tyr His Thr His Gly
               1205                1210                1215

Arg Tyr Val Pro Pro Ser Ser Thr Asp Arg Ser Pro Tyr Glu Lys Val
           1220                1225                1230

Ser Ala Gly Asn Gly Gly Ser Ser Leu Ser Tyr Thr Asn Pro Ala Val
       1235                1240                1245

Ala Ala Ala Ser Ala Asn Leu
   1250                1255


<210> SEQ ID NO 3
<211> LENGTH: 20
<212> TYPE: PRT
<213> ORGANISM: Homo sapiens
```

<400> SEQUENCE: 3

```
Pro Asp Thr Arg Pro Ala Pro Gly Ser Thr Ala Pro Pro Ala His Gly
  1               5                  10                  15

Val Thr Ser Ala
             20
```

<210> SEQ ID NO 4
<211> LENGTH: 24
<212> TYPE: PRT
<213> ORGANISM: Homo sapiens

<400> SEQUENCE: 4

```
Pro Thr Thr Thr Pro Pro Ile Thr Thr Thr Thr Thr Val Thr Pro Thr
  1               5                  10                  15

Pro Thr Pro Thr Gly Thr Gln Thr
             20
```

<210> SEQ ID NO 5
<211> LENGTH: 17
<212> TYPE: PRT
<213> ORGANISM: Homo sapiens

<400> SEQUENCE: 5

```
His Ser Thr Pro Ser Phe Thr Ser Ser Ile Thr Thr Thr Glu Thr Thr
  1               5                  10                  15

Ser
```

<210> SEQ ID NO 6
<211> LENGTH: 16
<212> TYPE: PRT
<213> ORGANISM: Homo sapiens

<400> SEQUENCE: 6

```
Thr Ser Ser Ala Ser Thr Gly His Ala Thr Pro Leu Pro Val Thr Asp
  1               5                  10                  15
```

<210> SEQ ID NO 7
<211> LENGTH: 8
<212> TYPE: PRT
<213> ORGANISM: Homo sapiens

<400> SEQUENCE: 7

```
Thr Thr Ser Thr Thr Ser Ala Pro
  1               5
```

<210> SEQ ID NO 8
<211> LENGTH: 29
<212> TYPE: PRT
<213> ORGANISM: Homo sapiens

<400> SEQUENCE: 8

```
Ser Ser Thr Pro Gly Thr Ala His Thr Leu Thr Met Leu Thr Thr Thr
  1               5                  10                  15

Ala Thr Thr Pro Thr Ala Thr Gly Ser Thr Ala Thr Pro
             20                  25
```

<210> SEQ ID NO 9
<211> LENGTH: 22
<212> TYPE: PRT
<213> ORGANISM: Homo sapiens

<400> SEQUENCE: 9

```
Thr Thr Ala Ala Pro Pro Thr Pro Ser Ala Thr Thr Pro Ala Pro Pro
  1               5                  10                  15

Ser Ser Ser Ala Pro Gly
             20


<210> SEQ ID NO 10
<211> LENGTH: 41
<212> TYPE: PRT
<213> ORGANISM: Homo sapiens

<400> SEQUENCE: 10

Thr Ser Cys Pro Arg Pro Leu Gln Glu Gly Thr Pro Gly Ser Arg Ala
  1               5                  10                  15

Ala His Ala Leu Ser Arg Arg Gly His Arg Val His Glu Leu Pro Thr
             20                  25                  30

Ser Ser Pro Gly Gly Asp Thr Gly Phe
         35                  40


<210> SEQ ID NO 11
<211> LENGTH: 21
<212> TYPE: PRT
<213> ORGANISM: Mus sp.

<400> SEQUENCE: 11

Met Glu Thr Asp Thr Leu Leu Leu Trp Val Leu Leu Leu Trp Val Pro
  1               5                  10                  15

Gly Ser Thr Gly Asp
             20


<210> SEQ ID NO 12
<211> LENGTH: 41
<212> TYPE: DNA
<213> ORGANISM: Mus sp.

<400> SEQUENCE: 12

ccaccatgga gacagacaca ctcctgctat gggtactgct g                         41


<210> SEQ ID NO 13
<211> LENGTH: 37
<212> TYPE: DNA
<213> ORGANISM: Mus sp.

<400> SEQUENCE: 13

tcctgctatg ggtactgctg ctctgggttc caggttc                              37


<210> SEQ ID NO 14
<211> LENGTH: 33
<212> TYPE: DNA
<213> ORGANISM: Mus sp.

<400> SEQUENCE: 14

tgctctgggt tccaggttcc actggtgacg atg                                  33


<210> SEQ ID NO 15
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15

ggttccactg gtgacgatgt cacctcggtc ccagtc                               36
```

<210> SEQ ID NO 16
<211> LENGTH: 31
<212> TYPE: DNA
<213> ORGANISM: Artificial Sequence
<220> FEATURE:
<223> OTHER INFORMATION: Description of Artificial Sequence: Synthetic primer

<400> SEQUENCE: 16
gagctcgaga ttgtggactg gaggggcggt g 31

<210> SEQ ID NO 17
<211> LENGTH: 51
<212> TYPE: DNA
<213> ORGANISM: Artificial Sequence
<220> FEATURE:
<223> OTHER INFORMATION: Description of Artificial Sequence: Synthetic primer

<400> SEQUENCE: 17
ccgctcgaga acgacgcaca agcaccaaaa tcaaaggtcg aagaggaagt a 51

<210> SEQ ID NO 18
<211> LENGTH: 53
<212> TYPE: DNA
<213> ORGANISM: Artificial Sequence
<220> FEATURE:
<223> OTHER INFORMATION: Description of Artificial Sequence: Synthetic primer

<400> SEQUENCE: 18
gcgggcccgc ggccgccgct agtctagaga gtttgagtaa gccaaaagat gag 53

<210> SEQ ID NO 19
<211> LENGTH: 10
<212> TYPE: PRT
<213> ORGANISM: Artificial Sequence
<220> FEATURE:
<223> OTHER INFORMATION: Description of Artificial Sequence: Synthetic spacer sequence

<400> SEQUENCE: 19

Leu Glu Asn Asp Ala Gln Ala Pro Lys Ser
1 5 10

<210> SEQ ID NO 20
<211> LENGTH: 62
<212> TYPE: DNA
<213> ORGANISM: Artificial Sequence
<220> FEATURE:
<223> OTHER INFORMATION: Description of Artificial Sequence: Synthetic primer

<400> SEQUENCE: 20
aacaagctca ttcagttcct gatctcactg gtgggatcca acgacgcaca agcaccaaaa 60
tc 62

<210> SEQ ID NO 21
<211> LENGTH: 60
<212> TYPE: DNA
<213> ORGANISM: Artificial Sequence
<220> FEATURE:
<223> OTHER INFORMATION: Description of Artificial Sequence: Synthetic primer

<400> SEQUENCE: 21
agccttcggc agaagcatgc ccagcaacag aaagtcgtca acaagctcat tcagttcctg 60

<210> SEQ ID NO 22
<211> LENGTH: 46
<212> TYPE: DNA
<213> ORGANISM: Artificial Sequence
<220> FEATURE:
<223> OTHER INFORMATION: Description of Artificial Sequence: Synthetic primer

<400> SEQUENCE: 22
aatgaggctc tgtggcggga ggtggccagc cttcggcaga agcatg 46

<210> SEQ ID NO 23
<211> LENGTH: 61
<212> TYPE: DNA
<213> ORGANISM: Artificial Sequence
<220> FEATURE:
<223> OTHER INFORMATION: Description of Artificial Sequence: Synthetic primer

<400> SEQUENCE: 23
gatatcctca ggctcgagaa cgacgcacaa gcaccaaaag agaatgaggc tctgtggcgg 60
g 61

<210> SEQ ID NO 24
<211> LENGTH: 53
<212> TYPE: PRT
<213> ORGANISM: Artificial Sequence
<220> FEATURE:
<223> OTHER INFORMATION: Description of Artificial Sequence: Synthetic amino acid sequence

<400> SEQUENCE: 24

Leu Glu Asn Asp Ala Gln Ala Pro Lys Glu Asn Glu Ala Leu Trp Arg
1 5 10 15

Glu Val Ala Ser Phe Arg Gln Lys His Ala Gln Gln Gln Lys Val Val
20 25 30

Asn Lys Leu Ile Gln Phe Leu Ile Ser Leu Val Gly Ser Asn Asp Ala
35 40 45

Gln Ala Pro Lys Ser
50

<210> SEQ ID NO 25
<211> LENGTH: 9
<212> TYPE: PRT
<213> ORGANISM: Artificial Sequence
<220> FEATURE:
<223> OTHER INFORMATION: Description of Artificial Sequence: Synthetic linker sequence

<400> SEQUENCE: 25

Leu Glu Asn Asp Ala Gln Ala Pro Lys
1 5

<210> SEQ ID NO 26
<211> LENGTH: 8
<212> TYPE: PRT
<213> ORGANISM: Artificial Sequence
<220> FEATURE:
<223> OTHER INFORMATION: Description of Artificial Sequence: Synthetic linker sequence

<400> SEQUENCE: 26

Asn Asp Ala Gln Ala Pro Lys Ser
1 5

<210> SEQ ID NO 27
<211> LENGTH: 51
<212> TYPE: DNA
<213> ORGANISM: Artificial Sequence
<220> FEATURE:
<223> OTHER INFORMATION: Description of Artificial Sequence: Synthetic primer

<400> SEQUENCE: 27
ccgctcgaga acgacgcaca agcaccaaaa tcaaaggtcg aagaggaagt a 51

<210> SEQ ID NO 28
<211> LENGTH: 51
<212> TYPE: DNA
<213> ORGANISM: Artificial Sequence
<220> FEATURE:
<223> OTHER INFORMATION: Description of Artificial Sequence: Synthetic primer

<400> SEQUENCE: 28
atggtgatga tgaccggtac ggagtttgag taagccaaaa gatgagaagc c 51

<210> SEQ ID NO 29
<211> LENGTH: 49
<212> TYPE: DNA
<213> ORGANISM: Artificial Sequence
<220> FEATURE:
<223> OTHER INFORMATION: Description of Artificial Sequence: Synthetic primer

<400> SEQUENCE: 29
gtgctctaga tcagaattca tggtgatggt gatgatgacc ggtacggag 49

<210> SEQ ID NO 30
<211> LENGTH: 60
<212> TYPE: DNA
<213> ORGANISM: Artificial Sequence
<220> FEATURE:
<223> OTHER INFORMATION: Description of Artificial Sequence: Synthetic primer

<400> SEQUENCE: 30
ccgctcgaga acgacgcaca agcaccaaaa tcagtgtatc ttcatagaag gttggacaag 60

<210> SEQ ID NO 31
<211> LENGTH: 34
<212> TYPE: DNA
<213> ORGANISM: Artificial Sequence
<220> FEATURE:
<223> OTHER INFORMATION: Description of Artificial Sequence: Synthetic primer

<400> SEQUENCE: 31
ccctctagat cagagtttga gtaagccaaa ggac 34

<210> SEQ ID NO 32
<211> LENGTH: 26
<212> TYPE: PRT
<213> ORGANISM: Homo sapiens

<400> SEQUENCE: 32

```
Met Ala Thr Gly Ser Arg Thr Ser Leu Leu Leu Ala Phe Gly Leu Leu
  1               5                  10                  15

Cys Leu Pro Trp Leu Gln Glu Gly Ser Ala
             20                  25
```

-continued

```
<210> SEQ ID NO 33
<211> LENGTH: 20
<212> TYPE: PRT
<213> ORGANISM: Homo sapiens

<400> SEQUENCE: 33

Pro Asp Asn Lys Pro Ala Pro Gly Ser Thr Ala Pro Pro Ala His Gly
 1              5                  10                  15

Val Thr Ser Ala
            20
```